(12) United States Patent
Falcone et al.

(10) Patent No.: US 9,381,271 B2
(45) Date of Patent: *Jul. 5, 2016

(54) CARBOXYMETHYLCELLULOSE POLYETHYLENE GLYCOL COMPOSITIONS FOR MEDICAL USES

(71) Applicant: FzioMed, Inc., San Luis Obispo, CA (US)

(72) Inventors: Samuel J. Falcone, Morro Bay, CA (US); Richard A. Berg, Arroyo Grande, CA (US)

(73) Assignee: FZIOMED, INC, San Luis Obispo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/887,717

(22) Filed: Oct. 20, 2015

(65) Prior Publication Data

US 2016/0038634 A1 Feb. 11, 2016

Related U.S. Application Data

(60) Division of application No. 14/313,151, filed on Jun. 24, 2014, now Pat. No. 9,161,987, which is a continuation of application No. 11/998,048, filed on Nov. 28, 2007.

(51) Int. Cl.

| | |
|---|---|
| *C08L 1/00* | (2006.01) |
| *A61L 27/20* | (2006.01) |
| *A61F 2/44* | (2006.01) |
| *A61L 27/50* | (2006.01) |
| *A61L 27/54* | (2006.01) |
| *A61L 31/04* | (2006.01) |
| *A61L 31/14* | (2006.01) |
| *A61L 31/16* | (2006.01) |
| *C08B 11/20* | (2006.01) |
| *C08L 1/28* | (2006.01) |
| *A61K 47/48* | (2006.01) |
| *A61L 27/58* | (2006.01) |
| *A61L 31/06* | (2006.01) |
| *A61F 2/30* | (2006.01) |

(52) U.S. Cl.
CPC ............ *A61L 27/20* (2013.01); *A61F 2/441* (2013.01); *A61K 47/48215* (2013.01); *A61L 27/50* (2013.01); *A61L 27/54* (2013.01); *A61L 27/58* (2013.01); *A61L 31/042* (2013.01); *A61L 31/06* (2013.01); *A61L 31/14* (2013.01); *A61L 31/148* (2013.01); *A61L 31/16* (2013.01); *C08B 11/20* (2013.01); *C08L 1/286* (2013.01); *A61F 2002/30062* (2013.01); *A61F 2002/3068* (2013.01); *A61F 2002/30224* (2013.01); *A61F 2002/30242* (2013.01); *A61F 2002/30581* (2013.01); *A61F 2002/30677* (2013.01); *A61F 2002/444* (2013.01); *A61F 2002/448* (2013.01); *A61F 2002/4435* (2013.01); *A61F 2210/0004* (2013.01); *A61F 2230/0071* (2013.01); *A61F 2250/0068* (2013.01); *A61L 2400/06* (2013.01); *A61L 2400/10* (2013.01); *A61L 2430/02* (2013.01); *Y10T 428/2982* (2015.01)

(58) Field of Classification Search
USPC .................................... 523/113, 115; 527/300
See application file for complete search history.

(56) References Cited

U.S. PATENT DOCUMENTS

| | | | | |
|---|---|---|---|---|
| 6,852,255 B2 * | 2/2005 | Yang | ..................... | C08B 15/005 264/186 |
| 6,869,938 B1 * | 3/2005 | Schwartz | ............... | A61K 47/10 514/42 |
| 7,166,570 B2 * | 1/2007 | Hunter | ................... | A61B 17/11 514/21.92 |
| 2007/0184087 A1 * | 8/2007 | Voigts | ..................... | A61L 27/20 424/423 |

* cited by examiner

*Primary Examiner* — Tae H Yoon
(74) *Attorney, Agent, or Firm* — D. Benjamin Borson; Borson Law Group, PC

(57) ABSTRACT

Uses of compositions comprising carboxypolysaccharides (CPS) including carboxymethyl cellulose (CMC) and polyethylene glycols (PEGs) are provided where the PEG is a PEG-epoxide covalently linked to the CPS in the presence of $NH_4OH$. In certain embodiments, the PEG attaches to only one CPS, forming a decorated CPS. In other embodiments, bi-functional PEG molecules are attached to adjacent CPSs, thereby forming a covalently cross-linked composition. Such compositions can be used as space-filling materials, load-bearing materials, anti-adhesion compositions, drug delivery vehicles, and lubricants of tissues and medical instruments.

10 Claims, 17 Drawing Sheets

CARBOXYMETHYLCELLULOSE POLYETHYLENE GLYCOL COMPOSITIONS FOR MEDICAL USES

CLAIM OF PRIORITY

This Application is a Division of U.S. patent application Ser. No. 14/313,151, filed Jun. 24, 2014 entitled "Carboxymethylcellulose Polyethylene Glycol Compositions for Medical Uses," Samuel J. Falcone and Richard A. Berg, Inventors, now U.S. Pat. No. 9,161,987, Issued Oct. 20, 2015, which is a Continuation of U.S. patent application Ser. No. 11/998,048 filed Nov. 28, 2007 entitled "Carboxymethylcellulose Polyethylene Glycol Compositions for Medical Uses," Samuel J. Falcone and Richard A. Berg inventors. These applications and patent are herein incorporated fully by reference.

FIELD OF THE INVENTION

This invention relates to compositions comprising derivatized carboxypolysaccharides (CPSs), and in particular, carboxymethylcellulose (CMC). Specifically, this invention relates to CMC derivatized with polyethylene glycols (PEGs) to form: (1) PEG-decorated CMC, (2) PEG ester-linked to CMC under acid catalysis, (3) PEG ester-linked to CMC under basic catalysis, and (4) PEG-ether linked to CMC or CPSs, and (5) uses thereof as space filling compositions, load-bearing compositions, lubricants, for antiadhesion compositions and for dermal fillers.

BACKGROUND OF THE INVENTION

Carboxymethylcellulose (CMC) is a water soluble, biocompatible and bioresorbable semi-synthesized polysaccharide. The safety of commercially available CMC having high purity has been identified and approved by the Food and Drug Administration (FDA) for incorporation into many products. CMC is able to react with various polymers by way of electrostatic interaction, ionic cross-linking, hydrogen bonding, Van der Waals interactions, and physical interpenetration. Because of its safety, convenience and diversity of physicochemical properties, CMC has demonstrated applications in the pharmaceutical, food and cosmetic industries.

CMC is one type of carboxypolysaccharide (CPS). CPSs have also been used in the manufacture of implantable polymers. CPSs are polymers made of saccharide monomers in which some of the hydroxyl (—OH) groups are replaced with carboxyl groups (—COOH or COO—). Thus, CPSs such as CMC have some hydroxyl groups and some carboxyl groups present. Carboxylation can permit ionic interaction within a polymer chain or can permit interaction between polymer chains, thereby forming a gel. Such gels have been used for a variety of applications, including implantable medical polymers.

SUMMARY OF THE INVENTION

Aspects of this invention are based on the previously unknown understanding that prior implantable polymer materials exhibited undesirable properties depending upon the tissue in which they were placed. For example, in tissues that have a high inherent elasticity, placing a relatively inelastic polymer can result in stresses on the tissue and can lead to tissue damage and deterioration. Thus, we realized that matching elasticities of tissues and of implantable polymers placed near or within those tissues can improved biocompatability of the polymer material.

Other aspects of this invention are based on the novel understanding that prior compositions containing CMC or other carboxypolysaccharides (CPSs) cannot permit manufacture of implantable polymers having a sufficiently controllable or wide range of elasticity and have improved biocompatibility.

Thus, we developed new compositions containing CPSs either decorated with or cross-linked with bi- or multi-functional poly(ethylene) glycols (PEGs). In general, PEGs useful in the compositions of this invention will have a glycidyl ether moiety. The glycidyl ether moiety is an epoxide, which can form covalent bonds with another reactive group via an addition reaction, without formation of toxic byproducts. Such PEGS are herein termed "PEG-epoxides." PEG-epoxides may have one epoxide moiety, two expoxide moieties ("PEG diglycidyl ether; "PEGDGE") or may have three or more epoxide moieties ("multi-branch PEGs" or "multi-arm PEGs"). Multi-branch PEGS are PEGS in which in-chain carbon atoms have an epoxide moiety. Multi-arm PEGS are PEGS in which several PEG polymer chains are attached together via a "hub" moiety, with the PEG chains having one or more epoxide moieties. It can be appreciated that PEGs having one or more glycidyl ether moieties can be used to manufacture compositions in which PEGs can have increased numbers of cross-linking moieties.

In one series of embodiments, a bi-functional PEG, PEG diglycidyl ether (PEGDGE), can be reacted with CPSs under basic or acidic catalysis to form compositions having covalent cross-links between CPS polymer chains. It can be appreciated that multi-functional PEGS (e.g., bi-functional PEGs or PEGDGE; multi-chain PEGs or multi-branch PEGs can be used to form compositions having CPSs cross-linked with PEGs within-chain or between-chains by covalent bonds.

In some embodiments, a PEG-epoxide can form a covalent bond with either a hydroxyl group of the CPS thereby forming an ether linkage. In other embodiments, a PEG-epoxide can form a covalent bond with a carboxyl group of the CPS thereby forming an ester linkage.

In some embodiments, basic catalysis of PEG-epoxide and CPS in the presence of sodium hydroxide (NaOH) can produce compositions having reduced elasticity compared to prior art CMC compositions. These new materials can be characterized by having relatively high ether content and relatively low ester content. As the relative amount of PEG-epoxide is increased, the elasticity of the derivatized CPS can be decreased in a controllable fashion, permitting manufacture for the first time of implantable CPS-containing polymers having a desired and controlled elasticity.

In other embodiments, basic catalysis of a PEG-epoxide and CPS in the presence of ammonium hydroxide ($NH_4OH$) can produce materials having increased elasticity compared to prior art CPS-containing compositions. In some of these embodiments, the materials are characterized by having significant ester linkages.

In further embodiments, acid catalysis of a PEG-epoxide and CPSs can produce materials having increased elasticity compared to prior art compositions of CPSs.

In still other embodiments, if a relatively low amount of a PEG-epoxide can be used compared to the number of functional groups (hydroxyl groups and carboxyl groups) on the CPS, the PEG-epoxide can bind to only one functional group, thereby "decorating" the CPS monomer without substantial cross-linking between different CPS molecules. In other embodiments, using a higher amount of PEG-epoxide can result in either intra-chain or inter-chain cross-linking. Increasing the inter-chain cross-linking can increase elasticity of the material. Thus, by adjusting the relative ratios of PEG-epoxide and CPS, and by adjusting the conditions of catalysis (e.g., NaOH, NH$_4$OH or acidic catalysis), the elasticity of the resulting polymer material can be finely adjusted to match the elasticity of the tissue in which the polymer is to be implanted.

Additional aspects include use of multi-arm or multi-branch PEGs, which can have multiple reactive epoxide moieties thereon. Use of such multi-arm and/or multi-branch PEGs can provide gels with more cross-linking per unit of CPS, and therefore higher elasticity than materials made with PEGDGE (a "bi-functional" PEG).

Further, in other aspects, CMC/PEG gels can be made and polymerized in situ without further precipitation and/or purification steps. Embodiments of these aspects can be useful where ease of manufacture is desirable.

The new compositions find use in a variety of medical and other applications. Compositions containing such PEG-CPS linked materials can be formed into membranes or into gels for antiadhesion uses, either during primary surgery or to decrease re-adhesion during corrective surgery, for long-term hydrogel implants, and for disk replacement. Manufacture of such membranes, beads, particulates, coatings and gels and some of their uses has been described in U.S. Pat. Nos. 5,096,997, 6,017,301, 6,034,140, 6,133,325, 6,566,345, 6,869,938 and 7,192,984, each patent expressly incorporated herein fully by reference as if individually so incorporated.

Compositions of this invention can be useful for delivering drugs to tissues. The sites of delivery of drugs using the compositions of this invention include, without limitation, skin, wounds, mucosa, internal organs, endothelium, mesothelium, epithelium. In certain embodiments, buccal, optical, nasal, intestinal, anal, vaginal applications using compositions of this invention can be used.

BRIEF DESCRIPTION OF THE FIGURES

The invention will be described with respect to the particular embodiments thereof. Other objects, features, and advantages of the invention will become apparent with reference to the specification and drawings in which:

FIG. 15a depicts an embodiment of this invention in which a cylindrical bag has a PEG/CPS composition therein.

FIG. 15b depicts an embodiment of this invention in which a spherical bag has a PEG/CPS composition therein.

FIG. 16a depicts a top view of a vertebra showing a vertebral body, annulus and a PEG/CPS-filled bag therein as a replacement for the nucleus pulposus.

FIG. 16b depicts a side view of two adjacent vertebrae, showing an intervertebral space with a PEG/CPS-filled bag as a replacement for the nucleus pulposus surrounded by an annulus.

FIG. 17a depicts a top view of a vertebra with a plurality of PEG/CPS-filled bags within an annulus.

FIG. 17b depicts a side view of two adjacent vertebrae, showing an intervertebral space with a plurality of PEG/CPS-filled bags within an annulus.

DETAILED DESCRIPTION

Definitions

Figure 1:
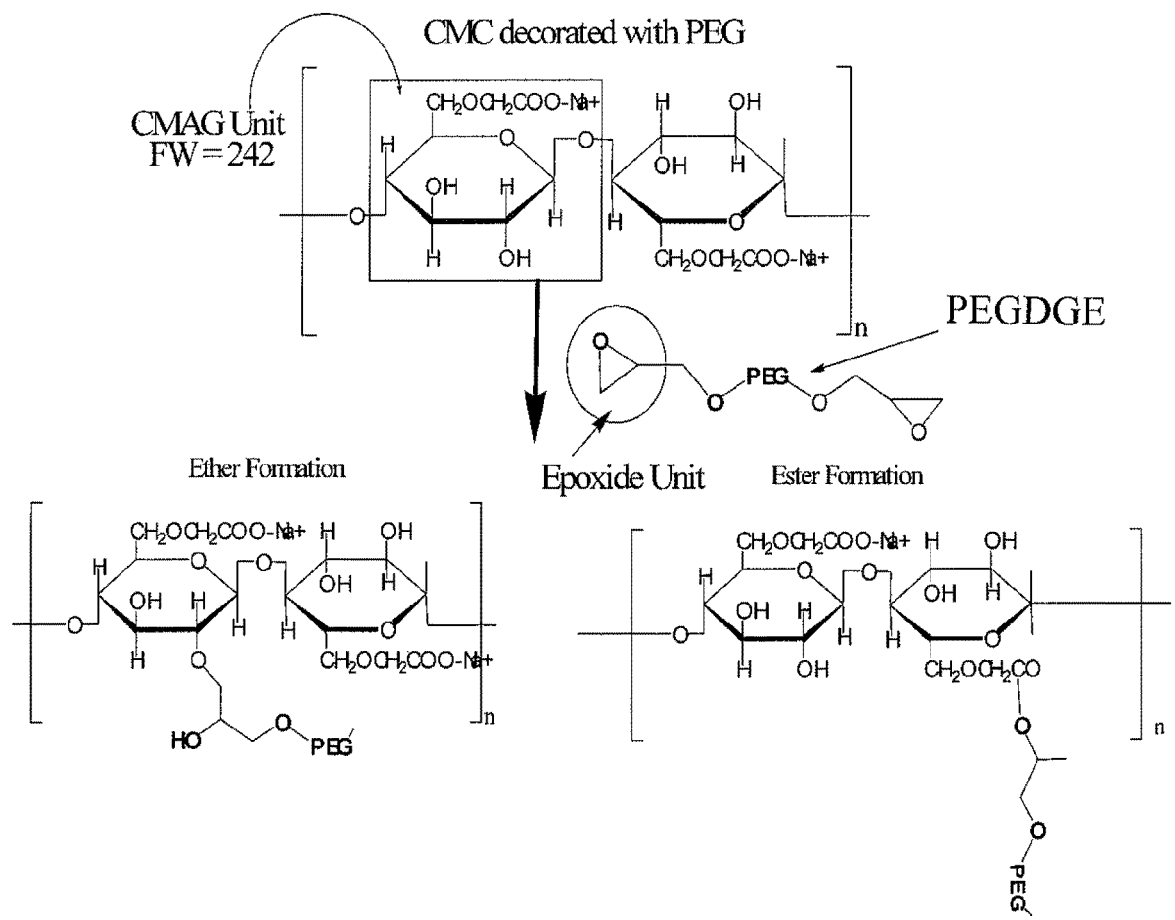
FIG. 1 is a diagram depicting decoration of a CMC polymer with PEGDGE and forming either an ether or an ester bond.

The following definitions apply in general to the descriptions that follow. In certain cases, however, a term may be defined differently. In those cases, the proper definition will be provided.

The term "cross-linking" or "crosslinking" means covalent bonding of two polysaccharide chains together using a chemical reagent.

The term "decoration" means covalent bonding of a chemical reagent to a single polysaccharide chain.

The term "CMC" means sodium carboxymethylcellulose. "CMC A" is Hercules CMC grade 7H PH lot #82666. "CMC B" is Hercules grade 9M31F PH lot #90252. "CMC C" is Hercules grade 7H PH lot #92013.

The term "cross-linker" or "crosslinker" means a chemical agent used in the covalent bonding of two polysaccharide chains to one another.

The term "PEO" means polyethylene oxide, a polymer made up of repeating units of compounds containing —(O—$CH_2$—$CH_2$)—. PEOs have molecular weights of greater than about 5000 kDa.

The term "Dalton" or "D" means a unit of molecular mass, where one D is equivalent to the mass of a proton.

The term "PEG" or "polyethylene glycol" means a polymer made of repeating units of compounds containing —(O—$CH_2$—$CH_2$)— but having molecular weights in the range of about 200 Daltons to about 5000 kDa.

The term "epoxide" means an organic functional group with an oxygen atom bonded to two adjacent carbon atoms, which has a chemical formula: —CH(O)$CH_2$. An epoxide is also herein termed a "glycidyl ether." An epoxide is a very reactive functional group that can be used in cross-linking or decoration reactions.

The term "glycidyl ether" means an organic functional group that contains the moiety: —CH(O)$CH_2$. An example is poly(ethylene) glycol diglycidyl ether (PEGDGE), a crosslinker used in embodiments of this invention. It should be appreciated that multi-branched PEGs and multi-arm PEGs are included within the meaning of "glycidyl ether."

The term "hydrogel" means a polymer matrix that swells in water but does not dissolve in water.

The term "ether linkage" means an organic functional group composed of a carbon-to-oxygen-to-carbon bond. An example contains a C—O—C linkage.

The term "ester linkage" as used herein for polymerization means an organic functional group composed of a O═C—R group, where R is a polymer.

The term "transmural pressure" means the hydrostatic pressure inside the sac minus the hydrostatic pressure outside the sac.

The term "Laplace's laws" refer to two relationships between transmural pressure, radius of a containment device (e.g., a "bag" or a "sac") and the wall stress. For a sphere, the wall tension "T"=Pressure "P" times Radius "R," or T=PR. For a cylinder, T=PR/2.

The term "viscosity" refers to a liquid-like property of a material having a relatively high resistance to flow in response to an applied force. Viscosity is a measure of the viscous, or liquid-like, nature of the material.

The term "Storage Viscosity" (G'/ω) is the elastic modulus G' divided by the frequency (ω), The term "Dynamic Viscosity" (G"/ω) is the loss modulus (G") divided by the frequency (ω).

The term "viscoelastic" means a property of polymeric materials that have both elastic (solid-like) and viscous (liquid-like) properties.

The term "elasticity" means a rheological property defined as the contribution of the elastic modulus, G', to the overall stiffness of the material. Elasticity includes Percent Elasticity as a specific example.

The term "Percent Elasticity" is defined as to be equal to: 100*G'/(G'+G").

The term "pseudoplastic" means a rheological property of some polymer solutions characterized by a decrease in solution viscosity at increasing shear rates.

The term "thixotropy" means a rheological property of some polymer solutions characterized by a time-dependent decrease in solution viscosity at a constant shear.

The term "Fourier Transform Infrared Spectroscopy," "FTIR Spectroscopy" or "FTIR" means an analytical technique that is used to detect various organic functional groups such as esters, ethers, etc. FTIR is based on absorbance of infrared electromagnetic radiation by molecules (such as functional groups).

The term "carboxymethyl anhydroglucose unit" or "CMAG unit" or "CMAG" is an individual repeat unit of a polysaccharide polymer chain.

The term "CMAG/EP ratio" or "CMAG/EP" means the ratio of CMAG equivalents to epoxide equivalents in the cross-linking reaction.

The term "Multi-Arm PEG" refers to PEGs that are formed around a core molecule permitting multiple PEG molecules to be covalently bonded to the core. A multi-arm PEG includes a 4-arm PEG, a 6-arm PEG or any PEG having multiple PEGs attached to a core molecule.

The term "Multi-Branch PEG" refers to a single PEG polymer having in-chain epoxide moieties attached thereto. Multi-branched PEGs may be characterized by having a particular ratio of epoxide:ethylene oxide moieties. A fully derivatized multi-branch PEG will have an epoxide:ethylene oxide ratio of 2. However, it should be understood that multi-branch PEGs may have epoxide:ethylene oxide ratios of less than 2, and that the ratio, on average, need not be integral in a plurality of PEG molecules.

The term "phosphate buffered saline" or "PBS" means a solution of water containing a phosphate buffer.

The term "base catalysis" means a chemical reaction that is speeded up or enhanced in the presence of a base.

The term "acid catalysis" means a chemical reaction that is speeded up or enhanced in the presence of an acid.

The term "ionic cross-linking" or "ionic crosslinking" is a method of combining constituents through ionic bonds.

DESCRIPTIONS OF SPECIFIC EMBODIMENTS

The descriptions of specific embodiments is intended to illustrate aspects of this invention, and is not intended to limit the scope of this invention. It can be appreciated that other applications of the compositions described herein can be developed by persons of ordinary skill in the art without undue experimentation. All of those embodiments are considered part of this invention.

PEG/CMC Compositions

This invention includes a variety of compositions having CMCs and PEGs, linked with ether or ester bonds. CMCs are polymers composed of sugar residues linked together, and each of which may have a carboxyl residue attached to the sugar moiety. There are three (3) potential sites for carboxylation on each sugar residue of CMC. Because a carboxyl residue can be chemically reactive, those locations on CMC are potential sites for derivatization. By controlling the degree of substitution ("DS" or "ds") of the CMC, the number of active groups on the derivatized CMC can be controlled.

FIG. 1 depicts CMC and PEG components of this invention. The portion of CMC shown includes two cellobiose units (each CMAG Unit having a FW of 242 Daltons). A PEGDGE molecule is shown with two epoxide units shown (one circled). PEG can be linked to the CMAG Unit either via ether linkage (bottom left) or an ester linkage (bottom right).

Figure 2:
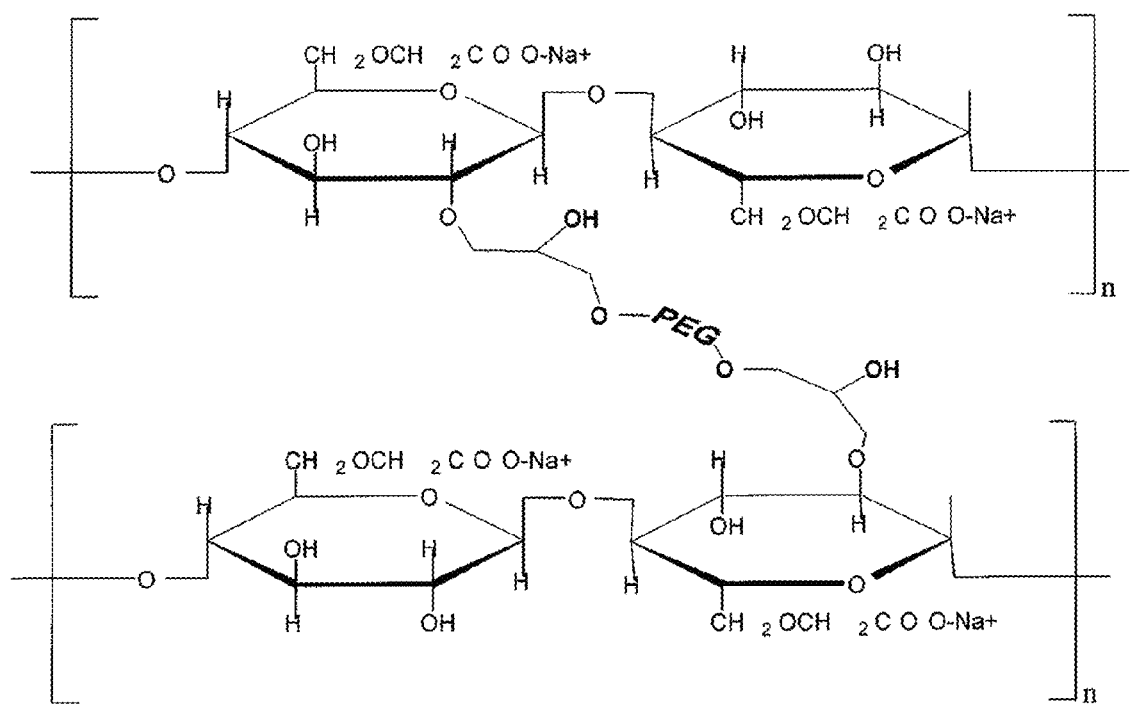
FIG. 2 is a diagram depicting inter-chain cross-linking of CMC polymers with PEGDGE via two ether linkages of this invention.

FIG. 2 depicts CMC with PEG cross-linking via ether linkages. Each end of the PEG molecule is shown bonded to a hydroxyl group of adjacent CMC molecules.

Uses of PEG/CMC Compositions

PEG/CMC compositions of this invention can be used for one or more of the following:

(1) as space filling materials, including those suitable for implantation as load-bearing compositions placed at locations where compressive loads may occur, such as in the spinal cord, for augmentation or replacement of the nucleus pulposus;

(2) as delivery vehicles for controlled release of bioactive substances, such as drugs, growth factors, active peptides, genes, cells, clotting factors such as thrombin, and antibiotics hormones including epinephrine, steroids, anti-inflammatory agents and the like, and vasoconstrictors such as norepinephine and the like;

(3) as delivery vehicles for the localized release of bioactive substances, such as drugs, growth factors, active peptides, genes, cells, clotting factors such as thrombin, and antibiotics, hormones including epinephrine, steroids, anti-inflammatory agents and the like, and vasoconstrictors such as norepinephine and the like;

(4) as binders for protein coupling and fatty absorption in both tissue engineering and food industries;

(5) lubrication of joints and medical instruments;

(6) tissue coating and tissue protection from fibrosis, neurotoxins, inflammatory mediators, free radicals and other harmful materials;

(7) anti-adhesion compositions; and (8) as dermal fillers;

Useful properties include, but are not limited to bioadhesion, bioresorbability, antiadhesion, viscosity, and physical interpenetration.

Preparation of PEG/CMC Compositions

The PEG/CMC compositions of this invention can be prepared into one or more of several forms, including gels, membranes, beads, sponges and coatings.

The technology to link CMC and other CPSs with PEG epoxides has wide potential for medical devices and includes two types of compositions. One includes methods to decorate CMCs with PEGs without cross-linking CMC molecules together. Another includes methods to cross-link CMC molecules together using PEG-epoxides. Reactions of CMCs with a PEG-epoxide is an addition reaction and therefore produces no known toxic by-products. Un-reacted PEG-epoxides can be hydrolyzed to PEG diols, which are known to be biologically compatible.

In contrast, some prior art cross-linking agents can produce undesirable side products. For example carbiodiimide can cross-link polymers, but because their reaction is not a simple addition reaction, reactive by-products are typically produced, which can react with tissues to produce unwanted side effects. Such side effects can cause serious side effects, especially in uses where the polymer composition is intended to remain in place for prolonged periods of time.

Similarly, other prior art cross-linking agents can exhibit unwanted side effects. For example, acrylates such as diacrylate, dimethacrylate, diacrylamide and dimethacrylamide all produce reactive by-products, in some cases, highly toxic by-products. Similarly, hydrazides, tosylates, thiol-containing CPSs (such as thiolated HA) and photoactivatable cross-linkers generally produce toxic by-products, thereby limiting their biocompatibility.

The types of CPSs that can be included in this invention is not limited to CMC. Rather, carboxyethyl cellulose (CEC), hydroxymethyl cellulose, cellulose and other cellulose derivatives.

Compared to prior art CPSs, CMC can be particularly useful in situations where it is desired that the residence time of the CPS in tissue be increased. For example, hyaluronic acid (HA) is a common CPS present in many tissues. HA has been used for implantable compositions, but HA can be degraded by tissue enzymes more readily than CMC. CMC is highly biocompatible, with little, if any, known side effects, and is well tolerated, even after prolonged exposure to tissues.

Space Filling Materials

PEG/CMC compositions of this invention can be particularly useful to fill voids in tissues resulting from disease or injury. For example, removal of a tumor during a surgical procedure can result in a loss of tissue volume. In situations in which organ or tissue function depends on the shape of the organ or tissue, PEG/CMC compositions of this invention can be used to fill the void. Similarly, in injuries, such as excavating injuries in which tissue volume is lost, PEG/CMC compositions of this invention can be used to fill those voids.

Load-Bearing Materials

Additionally, in situations in which tissue volume is lost through degeneration or other causes, PEG/CMC (PEG/CPS) compositions of this invention can be used to decrease adverse effects of such tissue loss. In certain aspects, PEG/CMC compositions of this invention can be used in load bearing capacities. For example, voids in the bone ("bone voids") of a vertebral body (e.g., caused by surgical removal of a tumor or degeneration of a vertebral disk nucleus) can result in pain, loss of sensation and/or loss of motion or function, due in some cases, to compression of spinal nerves. PEG/CMC compositions can be made with varying degrees of cross-linking, and in cases in which there is a high degree of cross-linking, the compositions can support increased loads. To make such compositions, the CMC can be used having a lower molecular weight, so that higher concentrations of CMC may be used resulting in more ether and carboxyl groups available for cross-linking. Also, using PEG-epoxides having lower molecular weights, multi-arm PEGs, and/or multi-branch PEGs can increase the number of covalent cross-links ("cross-link density") in the matrix. As the cross-link density increases, the ability of the matrix to support a load can increase. Thus, in certain aspects, highly-cross-linked PEG/CPS compositions can be used as nucleus replacements or to fill other bone voids.

In certain of these embodiments, a PEG/CMC (or PEG/CPS) composition can be placed in a biocompatible sac or bag within the intervertebral space, other bone void where the disk and/or disk nucleus was present, or in other locations where containment of the composition of this invention is desired. A bag can be made of a silicone-based polymer, such as Silastic™ or another, less deformable material, such as Mylar™ or other suitable material. It can be desirable to use a bag that has sufficient strength to resist breakage under the loads expected to be placed on the bag. Additionally, because both the PEG/CPS composition and the wall tension (under Laplace's law) can resist a load, these embodiments can be used in situations in which relatively large loads are to be borne.

Thus, in some embodiments, a biologically compatible bag (which may have a "one-way" valve to permit introduction of material into the bag but won't permit unwanted loss of material) of an appropriate size to fit within the intervertebral space or other location can be inserted in a deflated condition. Such insertion can minimize trauma to the vertebral bodies and the annulus. Once inserted into place, a PEG/CPS cross-linked composition can be introduced into the bag using a needle. Once in the bag, the PEG/CPS composition can polymerize to form a load-bearing structure, thereby replacing the lost or damaged nucleus. In embodiments in which there is frank loss of bone (e.g., due to removal of a tumor), a PEG/

CPS composition can be formed to the desired shape (as determined by x-ray, CAT scanning, or other imaging method). The replacement PEG/CPS load bearing compositions generally can be surgically implanted. Alternatively, a biocompatible bag or sac can be inserted in a deflated condition as described above for nucleus replacement, and then filled with a PEG/CPS composition, which is then permitted to polymerize into the load-bearing material.

In some embodiments, multiple bags or sacs can be used. In particular, in situations in which high loads are to be expected (e.g., the knee, ankles or other lower extremities, or lower back), the use of multiple, small sacs can be employed to take advantage of the fact of the well-known Laplace relationship between transmural pressure, radius and wall stress of a closed sac. As used herein the term "transmural pressure" means the hydrostatic pressure inside the sac minus the hydrostatic pressure outside the sac. Thus, for a given transmural pressure, a sac having a smaller radius will have lower wall stress placed upon the sac. In contrast, a larger sac will have larger wall stress at the same transmural pressure because of the larger radius.

Based on the Laplace relationships (one for a sphere; T=PR and another for a cylinder; T=PR/2), in certain embodiments of this invention, one can use a series of small, cylindrical sacs, each inserted into the bone void and filled with PEG/CPS composition of this invention. It can be desirable to align the longitudinal axes of the small sacs in parallel with the expected load. Thus, during polymerization, the small sacs can support the load better than a single sac having larger radius.

Additionally, in situations in which the annulus is damaged, one can introduce one or more sacs in the intervertebral space, with one near the hole in the annulus. Thus, when filled, the sac near the hole in the annulus can effectively seal the hole and minimize further loss of intervertebral material. In other embodiments, smaller sacs can be inserted and filled (to support the load) and a larger "plug" sac can be introduced into the intervertebral space. If this plug sac is then inflated with PEG/CPS composition of this invention, the sac can effectively plug the hole in the annulus and thus prevent the smaller sacs from being extruded.

Vehicles for Controlled Delivery of Bioactive Substances

PEG/CMC compositions of this invention can be used to deliver drugs, biologicals, nutrients or other biologically active agents (bioactive substances) to an animal. PEG/CMC compositions can be made incorporating a bioactive substance therein to provide a controlled-release composition. In general, PEG/CMC compositions having more cross-links tend to retain bioactive substances more than compositions having fewer cross-links. Such is the case for bioactive substances that are released from a PEG/CMC composition by simple diffusion out of the PEG/CMC matrix. In some cases in which the bioactive substance is large (e.g., protein), the bioactive substance may be released by a combination of simple diffusion out of the PEG/CMC matrix and by release as the PEG/CMC matrix is degraded in the body.

Regardless of which type of release occurs, it can be appreciated that the release of bioactive agents can be controlled as desired by varying the composition of the PEG/CMC composition of this invention. It is not intended that the type of bioactive substance be limited. Rather, any bioactive substance whose release is desired to be controlled can be effectively delivered using PEG/CMC compositions of this invention.

Vehicles for Localized Release of Bioactive Substances

In situations in which local release of a bioactive substance is desired, a PEG/CMC composition of this invention can be useful. Such situations may apply during tissue healing after surgery, where localized trauma to tissues produces localized inflammation. Thus, a PEG/CMC composition of this invention may contain a vasoactive substance to control bleeding (e.g., a vasoconstrictor, such as norepinephrine) or to promote hemostasis (e.g., a clotting factor). PEG/CMC compositions of this invention can also be useful for localized delivery of toxic agents in chemotherapy. For example, after tumor resection surgery, it may be desired to administer locally to the site, a PEG/CMC composition having a chemotherapeutic agent incorporated therein. Such localized application may permit application of higher concentrations of anti-tumor medications at the site needed, while reducing systemic side effects of traditional intravenous injection.

Binders for Protein Coupling

Other uses include more general uses of proteins, fats and other biological substances, whether bioactive or not. Thus, proteins can be incorporated into space filling PEG/CMC compositions of this invention. Such proteins may include collagen, gelatin, of other proteins known in the art.

Lubricants

PEG/CMC compositions of this invention can be effective lubricants for medical instruments. In situations in which a medical instrument is inserted into a body, there is a likelihood of at least some tissue trauma resulting. Trauma, even slight trauma can cause tissue damage, and can result in unwanted effects. Such effects include bleeding, inflammation, adhesion formation or scarring. By coating a medical instrument with a PEG/CMC composition of this invention prior to insertion into the body, such trauma can be decreased.

Lubrication can be used for both acute and chronic uses. Thus, for an acute procedure, such as urethral catherization, a PEG/CMC composition of this invention can be used to decrease pain and other discomfort as well as ease insertion. By decreasing urethral trauma, use of PEG/CMC compositions of this invention can decrease post-catheterization side effects, including decreasing pain on urination, urethral adhesions, and decreased likelihood of infection.

PEG/CMC compositions of this invention can also be effective tissue lubricants. In situations in which tissues traumatize adjacent tissues (e.g., in joints), compositions of this invention can be used to decrease friction and thereby decrease localized trauma. Thus, by injecting a PEG/CMC composition into an affected joint, pain can be reduced. By reducing friction and pain, the usual cascade of inflammation can be inhibited. By inhibiting inflammation, secondary adverse effects of inflammation can be decreased. Such adverse effects can be mediated by macrophages, leukocytes, mast cells, eosinophils, and mononuclear cells among others, each of which can produce bioactive substances that can make the situation worse. For example, mast cells contain potent proteases (e.g., mast cell tryptase and mast cell chymotryptase) that can degrade normal tissue proteins. Additionally, a series of interleukins can be released from neutrophils, macrophages and other inflammatory cells. Interleukins can be potent chemoattractive molecules and can recruit other inflammatory cells locally to the area, and can thereby continue adverse side effects of tissue trauma. Finally, tissue trauma can activate neuropeptide-containing nerves (e.g., c-fibers) known to contain substance P, which is a potent stimulus of pain pathways. In addition to causing pain, substance P is a potent chemoattractant and stimulator of mast cells.

In certain embodiments, PEG/CPS compositions of this invention can be used to lubricate joints, such as those in the spine. In particular, PEG/CPS compositions can be used to lubricate facet joints between adjacent lateral spinous processes. Similarly, compositions of this invention are useful as lubricants for other joints, including the knee, shoulder, elbows, wrists, ankles and hips.

Tissue Coatings: Antiadhersion Compositions

PEG/CMC compositions of this invention have wide applicability as tissue coating agents. PEG/CMC compositions can be used as anti-adhesion preparations. Adhesions are unwanted attachments of a tissue with an adjacent tissue. Adhesions commonly occur after surgery in which tissues are damaged as a result of the surgery. Thus, PEG/CMC compositions of this invention can be effectively used to provide a physical barrier between tissues that would otherwise tend to adhere to each other. PEG/CMC compositions may be membranes, gels or sponges. Many anti-adhesion uses are described in U.S. Pat. Nos. 5,096,997, 6,017,301, 6,034,140, 6,133,325, 6,566,345, 6,869,938 and 7,192,984, each patent expressly incorporated herein fully by reference as if individually so incorporated.

Dermal Fillers

Augmentation of the skin can be an important factor in recovering from injury or for cosmetic purposes. For example, with normal aging, skin may become loose or creases can form, such as nasal-labial (nasolabial) folds. In the face, creases or lines may adversely affect a person's self esteem or even a career. Thus, there has been a need for compositions and methods that can diminish the appearance of creases or lines.

Further, there are situations in which loss of tissue can leave an indentation in the skin. For example surgical removal of a dermal cyst, lipoatrophy or removal of a solid tumor can result in loss of tissue volume. In other cases, injuries, such as gunshot wounds, knife wounds, or other excavating injuries may leave an indentation in the skin. Regardless of the cause, it can be desirable to provide a dermal filler that can increase the volume of tissue to provide a smoother or more even appearance.

Several compositions are available for such purposes. Collagen is often used as an injectable material for soft tissue augmentation. Additionally, numerous other materials, including proteins, fats, hyaluronic acid (HA), polyalcohols, and other polymers have been used as injectable dermal fillers. However, non-cross linked, hydrophilic polymers such as collagen, gelatin and HA have not performed well and must be covalently cross-linked to remain in place to be effective. One example is ZYDERM®, which is uncrosslinked bovine collagen, was not effective as a dermal filler unless it was first cross-linked with glutaraldehyde to convert it to ZYPLAST®. Similarly, HA has not been sufficiently effective as a space filling material when injected or implanted in the body unless it is first cross-linked.

Compositions of CMC and modified CMC have unique properties that allow such compositions to be injected into the skin to fill spaces and to provide support where support is desired. One example for needed support is dermal augmentation in the face where dermal and subdermal volume is lost due to aging. CMC has a unique property of being an elastic gel with unique physical properties such as dynamic, plastic and zero shear viscosity, tissue adhesiveness, cohesiveness and flow characteristics. In addition, it can achieve these properties without the requirement of covalent cross-linking. CMC is particularly unique because chemical modifications of CMC expand the number of physical properties that make it an ideal injectable polymer for human treatment. For example, change in the degree of substitution has a dramatic effect on thixotropy and on viscosity of the gel. Its biocompatability and viscoelastic properties make it uniquely useful for injection into human skin where it becomes a space filling, biocompatible polymer.

Other polymers tested for their ability to perform as space filling gels are polysaccharides that have been used for soft tissue filing are inferior to CMC. For example, HA must be cross-linked to cause it to function as an elastic gel. Cross-linking limits its ability to be injected through narrow gauge needles, because the cross-linking converts HA into particles. For example, RESTYLANE® is a product consisting of cross-linked HA in a compatible solution.

Proteins used for dermal augmentation, such as collagen, also must be cross-linked to perform well as dermal fillers. For example, ZYPLAST® is a cross-linked bovine collagen dermal filler.

CMC can be a carrier for additional material for additional material for the skin, including hydrogel polymers such as PEO and emulsions. CMC can be used to deliver drugs to the skin, such as antioxidants, retinol, vitamins and growth factors. Covalent cross-linking of polymers converts them into particles that diminish their ability to deliver additional polymers, liposomes, emulsions or other particulates.

Numerous substances have been tested over the years for augmenting soft tissue in the dermis in the face to improve cosmesis by filling depressions in the skin (Klein and Elson, *The History of Substances for Soft Tissue Augmentation*, Dermatological Surgery 26:1096-1105, 2000). This is an area that continues to be studied as there has been no clearly superior material or product (Hotta, *Dermal Fillers: The Next Generation*, Plastic Surgical Nursing 24(1):14-19, 2004). These fillers are prepared from several polymers including bovine collagen, porcine collagen, chicken or bacteria fermented HA, gelatin, all of which are cross-linked covalently to reduce their dissolution time or immunological reactions. Fillers also include autologous human collagen (cross-linked collagen from the patient), human cadaver dermis (cross-linked human collagen). Additional fillers are those that are insoluble in the dermis, including PMMA beads, dPTFE (expanded polytetrofluoroethylene), poly lactic acid, recombinant elastin, and thermoplastics that form gels when injected into humans (Klein and Elson, *The History of Substances for Soft Tissue Augmentation*, Dermatological Surgery 26:1096-1105, 2000). More recently, ceramic particles (U.S. Pat. No. 5,922,025) and also PMMA microspheres (Lemperle et al, *Migration Studies and Histology of Injectable Microspheres of Different Sizes in Mice*, Plast. Reconstr. Surg 113(5):1380-1390 (2004) have been used for soft tissue augmentation.

Dermal fillers are used to fill scars, depressions and wrinkles. Dermal filler substances have various inflammatory responses in the dermis including phagocytosis to foreign body reactions depending on the material (Lemperle et al., *Human Histology and Persistence of Various Injectable Filler Substances for Soft Tissue Augmentation*, Aesthetic Plast. Surg. 27(5):354-366; discussion 367 (2003). One goal of dermal fillers it to temporarily augment the dermis to correct the surface contour of the skin without producing an unacceptable inflammatory reaction, hypersensitivity reaction or foreign body reaction that causes pain, redness or excessive scar formation for a period of time.

One of the first materials to be used for dermal augmentation is ZYPLAST® derived form bovine collagen. A newer material used for this application is RESTYLANE® derived from bacteria-produced HA. Because challenges include both biocompatibility and persistence in the skin, new dermal fillers are compared to one of the existing products such as ZYPLAST® or RESTYLANE® (Narins et al., *A Randomized, Double-Blind, Multicenter Comparison of the Efficacy* and *Tolerabiliyt of Restylane Versus Zyplast for the Correction of Nasolabial Folds,* Dermatol. Surg. 29:588-595 (2003).

More recently, CMC has been used with polyethylene oxide (PEO) and multivalent ions to produce ionically linked materials (U.S. Pat. No. 7,192,984, incorporated herein fully by reference).

I General Methods

In the following section, manufacture of CMC/PEG compositions are presented.

However, it should be appreciated that CMC need not be the only CPS used. Rather, any CPS can be used in manufacture of PEG/CPS compositions in similar fashions without departing from the scope of this invention.

A. Manufacture of CPS/PEG Compositions

To manufacture CPS/PEG (or CMC/PEG) compositions of this invention, generally the CPS is dissolved in aqueous medium, such as water, saline, phosphate-buffered saline or other suitable medium. For example, dissolving CMC is aqueous media is generally accomplished by adding a pre-weighed amount of powdered, dry CMC into a vessel containing the medium with stirring, such as with a vortex mixer until the CMC is completely dissolved. In some embodiments, CMC can be present in a concentration of from about 1% by weight to about 30% by weight. In other embodiments, CMC can be present in a concentration of about 3% to about 15% by weight. The molecular weights of CMC can be in the range of from about 50,000 D to about 1,000,000 D, alternatively from about 90 kD to about 700 kD.

To react PEG with the CMC, a pre-weighed amount of PEG with epoxide moieties is added to the CMC solution under stifling, until the PEG is dissolved. Then a catalyst is added to initiate the reaction. Generally, the reaction is permitted to go to completion, and the CMC/PEG composition is precipitated from solution, dried, and then reconstituted in solution for analysis and/or use. In some embodiments, the solution can be a physiologically compatible solution, with biocompatible pH, ionic strength, and colloid osmotic pressure. It can be appreciated that single chain, multi branched, or multi-arm PEGs having epoxide moieties thereon can be used.

PEGDGE can be used in a concentration of about 0.01% to about 20%. The molecular weights of PEG can be in the range of 200 D to about 50,000 D, and in alternative embodiments from about 500 D to about 8000 D.

In certain embodiments, NaCl can be used in a concentration in the range of about 0.001% to about 10%, and alternatively from about 0.01 to about 5.0%. In certain embodiments, isotonic saline can be used (e.g., about 0.9%).

If desired, multivalent ions can be added to the solution to produce ionically linked materials. $CaCl_2*H_2O$ can be used in concentrations of from about 0.001% to about 50% and in alternatives, from about 0.01% to about 10%. In other embodiments, CMC/PEG compositions can be made in phosphate buffered saline.

Catalysts can be used to initiate cross-linking. For example, acetic acid and citric acid can be used. Citric acid can be used in a concentration of from about 0.001% to about 50%, or alternatively from about 0.01% to about 10%. Acetic acid can be used in a concentration of about 0.001% to about 100%, alternatively about 1% to about 20%. Base catalysis can be accomplished using NaOH in a concentration of about 0.001% to about 80%, alternatively about 5% to about 20%. $NH_4OH$ can be used in a concentration of about 0.001% to about 40%, alternatively from about 1% to about 20%.

Additionally, pH can be varied to produce compositions that have some hydrogen bonded components. Useful pH ranges can be in the range of about 6.0 to about 7.5. Adjusting pH can be accomplished by immersing a CMC/PEG composition in a buffer solution at the appropriate pH.

In other embodiments, CMC/PEG compositions can be used directly after mixing the CMC and PEG-epoxide together, without subsequent precipitation and reconstitution. Thus, a CMC/PEGDGE solution can be prepared and drawn into a syringe, the syringe can then be sterilized (e.g., using steam), and the cross-linking reaction can proceed. When the reaction has occurred, the resulting material can be instilled into a desired location through a small-gauge (e.g., 29 or 30 gauge) needle. In other embodiments, solutions of CMC and PEG can be sterilized before mixing.

It can be appreciated that in addition to PEGDGE, other PEG-epoxides can be used, in fashions similar to those used for PEGDGE. Thus, multi-arm PEGs, multi-branch PEGs, or PEG-epoxides having different molecular weights can be used without departing from the scope of this invention.

B. Rheological Methods

Once a CMC/PE composition is prepared, its viscoelastic properties can be readily determined using equipment and methods known in the art. Small deformation oscillation measurements were carried out with a Thermo Haake RS300 Rheometer, Newington, N.H., in the cone and plate geometry. All measurements were performed with a 35 mm/1° titanium cone sensor at 25° C. The elastic modulus, G', and loss modulus, G", were obtained over a frequency range of 0.628-198 rad/sec. Tan δ was calculated as G"/G'.

Sodium carboxymethylcellulose (CMC) was obtained from Hercules and poly(ethylene glycol) diglycidyl ether (PEGDGE) was obtained from Sigma-Aldrich Corporation. According to manufacturer, CMC A had an average Mn of ~700,000 Da and CMC B had a average Mn of ~200,000 Da. Rheological measurements were performed on gels prepared at 30 mg/ml solids concentration in BupH Modified Dulbecco's Phosphate Buffered Saline solution (PBS) purchased from Pierce Chemical (catalog No. 28374). The solutions were prepared by stirring or CMC into the PBS at room temperature for at least two hours. The resultant solutions were clear and colorless with no solids evident and thus were used without filtration.

CMC/PEG compositions can be sterilized using any conventional method, such as steam sterilization, irradiation or filtration.

C. Determination of Compressive Strength of PEG/CPS Compositions

To determine the compressive strength of PEG/CPS compositions, a suitably shaped piece of material (e.g., 1 inch×1 inch×0.25 inches) can be prepared and placed on a surface such as a table. Once polymerization has occurred, a load (e.g., a known weight) can be placed on the composition. The weights can be progressively increased until the composition fractures. Alternatively, a composition can be placed in a vise, with a pressure gauge inserted, and the load increased progressively until the composition fractures.

II Preparation of PEG-Derivatized CPS

CPSs can be derivatized with PEGs to form either non-cross linked materials ("decorated CPSs") or as cross-linked materials of this invention. As used herein for PEG, the term "decoration," "decorating" and like terms refer to covalent attachment of a PEG via one end of the PEG to one site on a CPS molecule. Because only one end of the PEG is attached to the CPS, the other end of the PEG is unbound. Decorated CPSs therefore, are not cross-linked to other CPS molecules nearby or to themselves via intra-CPS bonds. Thus, the CPS has side chains of PEG "decorating" the CPS molecule. In other embodiments, the CPS/PEG composition can be prepared so that intra-chain and/or inter-chain covalent bonding can occur.

To ensure that only one end of the linker is coupled to the CPS strand, one can use a molar excess (based on the degree of substitution of the CPS) of the CPS. For example, one can use a molar ratio of active carboxylic acid groups to linker in the range of about 20-about 50 to provide a high degree of non-cross-linked CPS or CMC. Alternatively, by using a lower molar ratio, relatively more cross-linking between CPS molecules can be achieved. In embodiments in which a highly-cross-linked CPS is desired, one can use a relatively low (e.g., from less than about 0.5 to about 20) molar ratio of carboxyl residues to linkers. It can be appreciated that using a molar excess of linker molecules in a solution containing non-constrained CPS molecules (e.g., a relatively dilute solution of CPS) can promote derivatization of CPS with little cross-linking. However, in situations in which CPS molecules are constrained (e.g., high CPS concentrations) or are tightly packed together, there may be an increased tendency for cross-links to form between different CPS chains. It can be readily appreciated that workers of skill in the art can select a molar ratio of carboxyl residues to linker molecules to produce a desired degree of cross-linked CPSs.

CPSs decorated with PEGs typically have lower elasticity and higher viscosity than un-decorated CPSs. Thus, CMC decorated with PEG can be more adherent to tissues, and additionally may be more useful in situations in which un-decorated CMC may have reduced biocompatability compared to PEG-decorated CMC.

A PEG Decorated CPS

In one series of embodiments, the glycyldyl ether moiety of PEG can react with either of the two types of reactive moieties on a CPX, namely, a hydroxyl or a carboxyl group. If PEG reacts with a hydroxyl group, the resulting molecule contains an ether linkage. In cases where the PEG bonds with a carboxyl group on a CPS, the resulting molecule contains an ester linkage.

In situations in which there is a molar excess of PEG relative to the number of reactive moieties on the CPS, the favored reaction is between one PEG and one CPS, without substantial intrachain crosslinking of the CPSs together. Such "PEG decorated CPSs" have particular usefulness for compositions in which the elasticity is relatively low, in contrast to crosslinked PEG/CPS compositions.

Decorating CMC with PEG can increase the biocompatability of the composition. Decorating CPS with PEG can also decrease the elasticity of the composition, because the derivatized material will have fewer free hydroxyls available (in a CPS with high degree of substitution, d.s.). With fewer reactive groups available, the thixotropy of the material will be also be decreased.

B. PEG Cross-Linked CPSs

In situations where a more elastic composition is desired, one can cross-link CPSs together using PEGDGE, in which the relative amounts of CPS and PEGDGE are more equal. In certain embodiments, one can use increased amounts of CPS relative to PEGDGE, thereby favoring reactions in which one PEGDGE molecule forms covalent bonds with two CPS molecules.

It can be appreciated that because of the two types of reactive moieties on a CPS (e.g., a carboxyl group and an ether group), PEG cross-linked CPSs can have either ester or ether linkages, or an ester link at one end of the PEG and an ether link at the other end of the PEG.

1. Effect of Acid or Basic Catalysis

We have also found that the reaction conditions can affect the types of reactions that occur. For example, acid catalyzed addition of PEGDGE to CPS can produce one type of cross-linked composition, whereas base catalyzed addition of PEGDGE to CPS can produce another type of cross-linked composition. Each of these two types of reactions produce PEG-cross-linked CPSs having desirable, different properties.

2. Multi-Functional PEGs

In addition to PEGDGE (a "bi-functional" PEG), multi-functional PEGs can be used. Multi-branch PEGs and multi-arm PEGs can be used to make CMC/PEG compositions having increased cross-linking. For example, use of these types of PEGs can permit more rapid polymerization. Thus, such materials can be prepared shortly before implantation, and after implantation, in situ cross-linking can occur to produce a longer-lasting, more elastic material. Such compositions can be particularly desirable in situations where a void is to be filled, or where a disk nucleus has become damaged and spinal nerves are impinged upon by vertebral bodies or spinous processes.

It can be appreciated that one can increase the elasticity and/or stiffness of a CMC/PEG composition by using more reactive species. It is known that increasing the MWs of CMCs (or CPSs) produces solutions having higher viscosity, and may thus be more difficult to manipulate. Conversely, decreasing the MW of the CMC can produce aqueous solutions having lower viscosities. One can increase the amount of cross-linking by using CMCs (or CPSs) having lower molecular weights. By using lower MW CMCs, one can increase the total mass of CMC that can be effectively dissolved while maintaining a solution viscosity sufficiently low to be easily manipulated. Thus, with the addition of an appropriate amount of PEG epoxide sufficient to provide a CMAG/EP ratio needed to produce a cross-linked composition having a desired elasticity, the reaction rate can be increased, permitting more easy preparation of materials.

3. In Situ Cross-Linking

Such rapid cross-linking reactions may be particularly desirable for use in situ, in locations where rapid administration is desired. In some embodiments, the components can be sterilized before use, and the final preparation can be prepared from sterile solutions. In these situations, a rapidly cross-reacting mixture can be prepared and then introduced into the site.

From the above discussion, there may be multiple ways of increasing the rate of cross-linking reactions. Increasing the amount of PEGDGE or multifunctional PEG, decreasing the MW of the CMC (or CPS), increasing the amount of initiator or catalyst can either alone or in combination, be used to produce compositions that can polymerize sufficiently rapidly to be useful for situations including use in load-bearing joints, excavating injuries, surgical procedures and the like. One can also use an in situ polymerizing composition to provide long-lasting dermal filling of the more conventional nature, such as filling nasolabial folds, crow's feet and other dermal lines.

1. Acid Catalysis

In certain embodiments, to produce acid-catalyzed products of CMC and PEG, we used the materials and conditions shown below in Table 1.

TABLE 1

Reaction conditions for acid catalyzed reaction of CMC with PEGDGE

| CMC | [CMC] mg/mL | Catalyst | CMAG mMol | EP mMol | CMAG/EP | Results |
|---|---|---|---|---|---|---|
| 82666 | 30 | 1% acetic acid 40° C. | 30.99 | 8.67 | 3.6 | Drastic increase in elasticity |
| 82666 | 30 | 0.01% Citric acid 40° C. | 30.99 | 2.17 | 14.3 | Elasticity increased |
| 90252 | 50 | 1% acetic acid 40° C. | 51.65 | 21.67 | 2.4 | Insoluble material too highly cross-linked |
| 90252 | 50 | 1% acetic acid 60° C. | 51.65 | 10.83 | 4.8 | Drastic increase in elasticity |
| 90252 | 50 | 1% acetic acid 0° C. | 51.65 | 2.17 | 23.8 | Elasticity decreased slightly |

It can be appreciated that the above reaction conditions are illustrative only, and other conditions (CPSs, acids, pH, ratios of CMAG/EP and the like) can be used to produce variations of the compositions of this invention that have variations in elasticity. In general, we found that using stronger acids (e.g., acetic acid) tended to produce compositions having increased elasticity. We also found that higher reaction temperatures tended to produce more elastic materials. Moreover, we found that using CMAG/EP ratios of below about 10, tended to produce compositions having greater elasticity than compositions made with higher ratios of CMAG/EP. However, using strong acid (e.g., acetic acid) at high temperature (e.g., 40° C.) and a very low ratio of CMAG/EP (e.g., 2.4) produced a composition that was so highly cross-linked that it was insoluble.

We also found that both reacted materials have slightly lower complex viscosity at low frequencies than the un-derivatized CMC. At high frequencies, the un-derivatized CMC had a much higher complex viscosity than the derivatized CMC. There are two components of the magnitude of the complex viscosity, the storage viscosity ($\eta"=G'/\omega$) and the dynamic viscosity ($\eta=G''/\omega$). We found that low frequencies, the dynamic viscosity is much higher for the un-derivatized CMC than for the derivatized CMC. This finding indicates that the loss modules G" is higher at low frequencies and has a greater contribution to the complex modulus at low deformation rates.

2. Base Catalysis

In certain embodiments, we react glycidyl ethers with CMC using base catalysis. In certain embodiments, sodium hydroxide (NaOH) and ammonium hydroxide (NH$_4$OH) can be used. We found that basic catalysis using NaOH produced cross-linked compositions having little ester, and were therefore predominately ether-linked compositions. These compositions have lower elasticity than the un-derivatized CMC. Base-catalyzed materials have in general, lower elasticity than un-derivatized CMC. The elasticity of the gel can be altered by adjusting the epoxide to hydroxyl ratio. As the ratio is decreased, elasticity increases. Conversely, as the epoxide content is increased, the elasticity of the composition decreases. In certain of these embodiments, highly-cross-linked compositions are not formed and the reaction produces PEG Decorated CMC.

In contrast, we found that base catalysis using NH$_4$OH produced compositions having some ester formation. NH$_4$OH catalyzed PEGDGE/CMC reactions produce compositions having reduced elasticity and are highly hydrated (swollen) hydrogels.

3. Neutral Catalysis

In situations in which it is undesirable to expose a tissue to either acidic or basic compositions, a PEG/CPS polymer can be made using neutral conditions. Epoxides can react with carboxyl groups or with ether groups under neutral conditions, although the rates of the polymerization reactions are typically shower than those initiated under either acidic or basic conditions. However, the rate of reaction can be increased by increasing the number of reactive moieties available for the reaction. Thus, using CPSs or PEGs having lower average molecular weights, using multi-branch PEGs, multi-arm PEGs or combinations of each of these components, one can produce polymer compositions with high degrees of cross-linking, and therefore, higher compressive strength and higher elasticity compared to compositions made with bi-functional PEGs and high molecular weight components.

C. Sterilization of CMC/PEG Compositions

As noted above, CMC/PEG compositions may be conveniently sterilized using heat. In some embodiments, the composition may be heated in an autoclave or other steam producing apparatus. In some cases, it can be desirable to prepare a CMC/PEG composition and then place it into a delivery device, such as a syringe. CMC/PEG compositions can be made using a "3-step" process, in which: (1) a CMC/PEG mixture is obtained, (2) an initiator is added to start the cross-linking reaction and (3) where the cross-linked material is precipitated and reconstituted. Alternatively, a CMC/PEG composition can be made using a "one-step" process, in which the CMC/PEG solution is made with an initiator and then placed in a delivery device for sterilization. In these situations, heating not only sterilized the composition, but it also increases the rate of cross-linking. After sterilization in situ, the CMC/PEG composition is ready to use.

III. Uses of CMC/PEG Compositions

CMC/PEG compositions of this invention can be used as space filling materials, delivery vehicles for bioactive substances, load-bearing materials, anti-adhesion compositions and/or lubricants for tissues, joints, medical instruments, dermal fillers, and other medical applications.

Space Filling Materials

In other embodiments, space filling materials can be used to provide bulk in internal locations. For example, in situations where a void has been created as a result of removal of internal tissue (e.g., removal of a sebacious cyst, bullet wound, removal of a localized tumor), in an area not subject to large movements (e.g., the torso), an implant can be made having a desired shape and having a desired elasticity. Such space filling materials, made according to the principles of this invention, can be highly biocompatible, having long residence times in the body. Such materials can be made in any particularly desired shape. Thus, if the void is irregular, the surgeon can shape the implant to match the void. After making a surgical incision through the skin, the implant is inserted and the wound sutured. Alternatively, the surgeon can inject a composition comprising a gel having particles of PEG/CMC material therein. After introduction into the void, the material can conform to the shape of the void, thereby providing a uniform appearing structure.

In still further embodiments, space-filling materials can be contained within a biocompatible sac. For example, one can insert a PEG/CMC cross-linked composition into the spine to provide support in situations where the nucleus of a vertebral disk has become damaged. By encasing PEG/CMC compositions within a sac, the implanted material can resist compressive forces, and therefore can be used to avoid nerve pinching, a common cause of pain in subjects with degenerating disks.

In still further embodiments, PEG/CMC materials of this invention can be dried to form membranes. As described in U.S. Pat. No. 5,906,997 (incorporated herein fully by reference), CPS/PEO membranes can be made by preparing a gel, and then drying the gel. Similar membranes can be made using PEG/CMC compositions of this invention.

Load-Bearing Materials

In additional aspects, PEG/CPS compositions can be used to support loads within the skeletal system. For example, the spine is often a location where degeneration, injury or disease can produce loss of structural support. In particular, in conditions in which the disk is damaged, PEG/CPS compositions of this invention can be readily used. In situations in which the nucleus pulposus is partially or completely lost, compositions of this invention can be used to replace the lost tissue. In some of these embodiments, an elastic, relatively non-compressible composition can be polymerized before insertion into the affected area. In other situations, one can administer a composition of this invention prior to its polymerization, so that the composition polymerizes in situ. For example, in situations in which there is frank loss of bone, producing an irregularly shaped defect, a mixture of components of this invention can be injected. After polymerization, the composition can fit well into the defect, thereby providing structural support.

In other situations, compositions of this invention can be placed within one or more bags or sacs. These embodiments can have increased load-bearing abilities, due to the facts that: (1) a composition can be supported against compression by the bag or sac, and/or (2) the composition has its own load-bearing abilities.

Figure 15A:
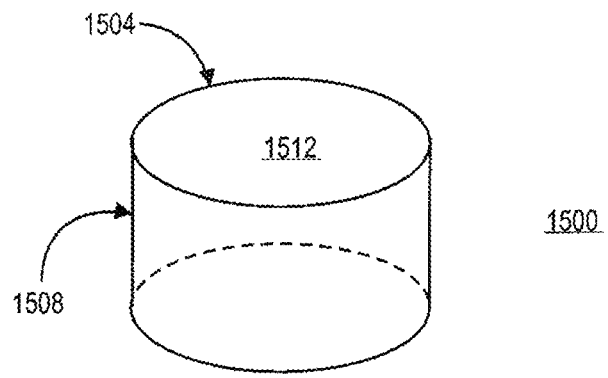
FIGS. 15a and 15b depict two embodiments of this invention, in which a PEG/CPS composition is enclosed in a bag.
Figure 15B:
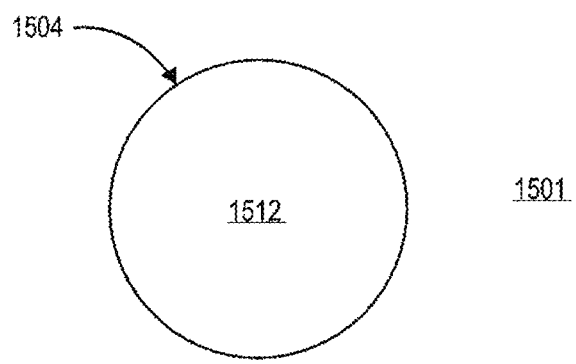

FIGS. 15a and 15b depict embodiments of this invention in which a PEG/CPS composition is placed within a bag or sac. FIG. 15a depicts an embodiment 1500 in which a top portion 1504 of the exterior and a side portion 1508 of the exterior define an enclosed space. In this embodiment, the PEG/CPS composition 1512 is depicted within the enclosed space. FIG. 15b depicts an alternative embodiment 1501 in which the exterior 1504 of the bag or sac has a spherical shape. PEG/CPS composition 1512 is shown within the space defined by the exterior 1504.

Antiadhesion Materials

In still further embodiments, compositions of this invention can be used as antiadhesion materials. Methods for using CMC compositions for antiadhesion purposes are described in U.S. Pat. Nos. 5,906,997, 6,017,301, 6,034,140, 6,133,325, 6,193,731, 6,869,938, and 7,192,984. Each of the aforementioned patents are expressly incorporated by reference as if separately so incorporated. It can be readily appreciated that gels, membranes and other forms of the CMC/PEG compositions of this invention can be used in similar ways.

Drug Delivery Using CMC/PEG Complexes

It can be readily appreciated that any number of drugs, biologicals and other chemical agents can be delivered using the CMC/PEG composites of this invention. Certain agents can be advantageously used for local delivery, providing desired concentration at a desired site, but while decreasing undesirable, systemic effects. Such agents include, but are not limited to therapeutic proteins, such as thrombin to aid in attaining and maintaining hemostasis, growth factors for bone, cartilage, skin and other tissue and cell types. Some of these peptide and protein growth factors include bone morphogenic protein (BMP), epidermal growth factor (EGF), connective tissue growth factor (CTGF), platelet derived growth factor (PDGF), angiotensin and related peptides, and RGD-containing peptides.

Additionally, locally acting drugs include fungicides, histamine, antihistamine, anti-inflammatory drugs (methotrexate), local anesthetics, angiogenesis promoting drugs (e.g., to treat cardiovascular disease, and anti-angiogenesis factors (e.g., to treat tumors).

DNA-based therapeutics, including antisense DNA, gene therapeutics and RNA-based therapeutics are also suitably delivered using the compositions of this invention. These agents can be used to either inhibit or promote transcription of endogenous genes, or alternatively, can provide exogenous gene products to promote local treatment.

Locally delivered chemotherapeutic agents can also be delivered. These include, by way of example only, antibiotics to treat microbial conditions, antifungal agents, antiparasitic agents, anti-neoplastic agents including alkylating agents, anti-metabolites and the like.

It can also be appreciated that various hormones and steroids can be delivered, as can other, systemically acting drugs, which can be delivered transmucosally or transdermally. These include IgG, clotting factors and enzymes for treating mucopolysaccharidosis or other conditions.

Cardiovascular drugs include vasodilators such as β-adrenoreceptor agonists including terbutaline and low-dose epinephrine, α-adrenoreceptor antagonists including norepinephrine, high-dose epinephrine and the like, and vasodilators including nitroprusside and nitroglycerin.

It can be appreciated that the above descriptions are not intended to be limiting to the scope of the invention. Rather, they are intended to be representative of the many different embodiments of the invention.

Lubrication of Joints

Certain aspects of this invention include use of PEG/CPS cross-linked compositions to provide lubrication for joints and soft tissues. In situations in which injury to bone, ligaments, tendons, fascia or other soft tissues has occurred, healing may not produce a smooth-functioning tissue. For example, damage to facet joints in the spine can result in abnormal alignment of vertebrae, which can lead to further damage to the disk (annulus or nucleus pulposus). Thus, a PEG/CPS composition of this invention can be injected between lateral spinous processes of adjacent vertebrae (which normally can slide past one another during normal movement). After such injection, the lateral spinous processes can be separated from each other, and the inherent lubrication afforded by the PEG/CPS composition can decrease further irritation.

In a similar fashion, damage to tendons, ligaments and fascias can produce pain, swelling and decreased function.

This, insertion of a PEG/CPS composition of this invention can improve mobility and can decrease the likelihood for further damage to the tissue.

Tissue Protection

PEG/CMC compositions can also be used to protect tissues from damage. For example, such compositions can protect peripheral nerves, tendons, ligaments, other soft tissues, synovial membranes, joints, and can thereby relieve pain.

For example, tendon and ligament injuries heal more slowly than to other tissues, in part because the blood flow to tendons and ligaments is reduced compared to tissues such as muscles, mesenteries, and the like. Furthermore, a tendon stress-related injury often is accompanied by a stress injury to an adjacent ligament. Therefore, healing of both tissues is required for a return to normal function. However, such recovery is often slow, and re-injury is common. Further, even when healed, tendons and ligaments tend to heal with scar tissue, which is not smooth. Thus, even after healing, a previously injured tendon or ligament may abrade adjacent tissues and cause either re-injury or slow recovery processes.

In another example, in the spinal cord, damaged spinous processes or vertebral bodies may abrade adjacent tissues. Additionally, loss of a vertebral nucleus can lead to compression of vertebral bodies and can result in impingement of spinal nerves, often leading to pain and/or paralysis.

A further example can involve damage to peripheral nerves, where soft tissue injury, trauma or inflammatory reactions can lead to pain or loss of nerve function. Application of a PEG/CMC composition of this invention can decrease inflammatory responses, and therefore can decrease secondary damage caused by inflammatory reactions mediated by, for example, macrophages, leukocytes, mast cells or other types of inflammatory cells.

Additionally, PEG/CMC compositions of this invention can be useful to minimize joint pain. In numerous conditions, including arthritis, traumatic injury, degeneration of cartilage, and ligament damage, a joint can become painful. A PEG/CMC composition of this invention can be introduced into an affected joint to provide lubrication and to protect adjacent tissues from damage caused by movement. For example, in the knee, a PEG/CMC composition can be introduced during an arthroscopic procedure. In situations in which the joint must bear a load (e.g., knee, hip, ankle, vertebra), a PEG/CMC composition can be made with particularly high elasticity.

Dermal Filling

Compositions of this invention are particularly well suited as dermal fillers. As noted above, one of the difficulties with prior art dermal fillers is mismatching of the elasticities of the tissue and the dermal filler. In situations where the tissue is relatively elastic and the dermal filler is relatively inelastic, lumps can appear where the tissue can stretch, but the dermal filler does not. Conversely, in situations in which the elasticity of the dermal filler is higher than that of the tissue, incomplete filling of voids can occur.

Thus, by selecting viscoelastic properties of a dermal filler to approximate or match the elasticity of the tissue, a better void-filling material can be produced and used, while minimizing adverse effects of tissue-filler mismatching.

Additionally, as an individual ages, the elasticity of the skin tends to decrease. Thus, in subjects with less elastic skin, one might desirably use a dermal filler with lower elasticity than one might use in a younger individual with more elastic skin. Similarly, certain tissues tend to have different elasticities or different mobilities. For example, the skin around facial muscles (e.g., nasolabial folds) may be subject to different stresses than other tissues (e.g., the lips). Thus, one can select dermal fillers having different viscoelastic properties for use in the same subject.

Use of such dermal fillers depends upon the specific need. For example, when used to fill small wrinkles, such as nasolabial folds, or "crow's feet" around the eyes, dermal fillers in the form of a uniform gel or small particles can be desired. An advantage of using a uniform gel is that these materials can be injected using very small needles, and can produce a very smooth filling, particularly well suited for smoothing small lines. For use in somewhat larger lines (e.g., nasolabial folds), it can be desirable to use compositions comprising a gel having particles of PEG/CMC. Such particles can be made according to methods known in the art, and can be made to have desired dimensions. For use in nasolabial folds, the particles should be sufficiently small to pass easily through a small needle (e.g., a 25 or 30 gauge needle). The remainder of the composition can be a PEG/CMC gel having relatively lower viscosity. After injection, the particles can further hydrate in the tissue, thereby forming a more uniform composition.

It can be appreciated that certain embodiments (e.g., "one-step") embodiments can provide easy to produce, pre-sterilized compositions in a suitable delivery device (e.g., syringe). Pre-made PEG/CMC compositions, having desirable elasticity, can be injected directly into the site using a small gauge (e.g. 25, 26, 27, 28, 29 or 30 gauge) needle.

In each of the above situations, PEG/CMC compositions of this invention can be beneficial.

EXAMPLES

The following examples are presented to illustrate certain embodiments of this invention, and are not intended to limit the scope to the embodiments so illustrated. Rather, workers of skill in the art can modify or adapt the teachings of this invention to make and use other variations without undue experimentation. All of those embodiments are considered to be part of this invention.

Example 1

Crosslinking of CMC a with PEGDGE at a CMAG/Epoxide Ratio of 0.8/1 in Dilute NaOH To a 400 ml polypentene beaker we added distilled, deionized water (DIW) (250 mL) and NaOH (2.5 g; 60.25 mM). After 5 minutes of stirring at 400 rpm, CMC A (5.0 g; 40.83 mM OH) was added and stifling continued for 35 minutes at 25° C. Subsequently, PEGDGE, (6.884 g; 6.0 mL; 8.7 mM) was added neat and stifling was continued at ambient temperature for 90 minutes. After that time, we then heated the mixture to about 70° C. for 1 hour and about 90° C. for 2 hours. The mixture was then cooled to ambient temperature overnight.

The solution was diluted to a volume of about 250 mL with DIW and neutralized with 3.5 ml of glacial acetic acid. At this point the pH was 5.3 and 20% NaOH was added to bring the pH to 6.8. The resulting polymer was precipitated with IPA, collected and then ground in a blender with isopropyl alcohol/methanol (IPA/MeOH) 1:1 in a volume of about 250 mL. The granular solid was collected and washed three times with about 50 mL of acetone then dried in a hood for 20 minutes and the dried in vacuum at a temperature of about 80° C. For rheological testing, the dried composition was reconstituted in phosphate-buffered saline (PBS).

Figure 3:
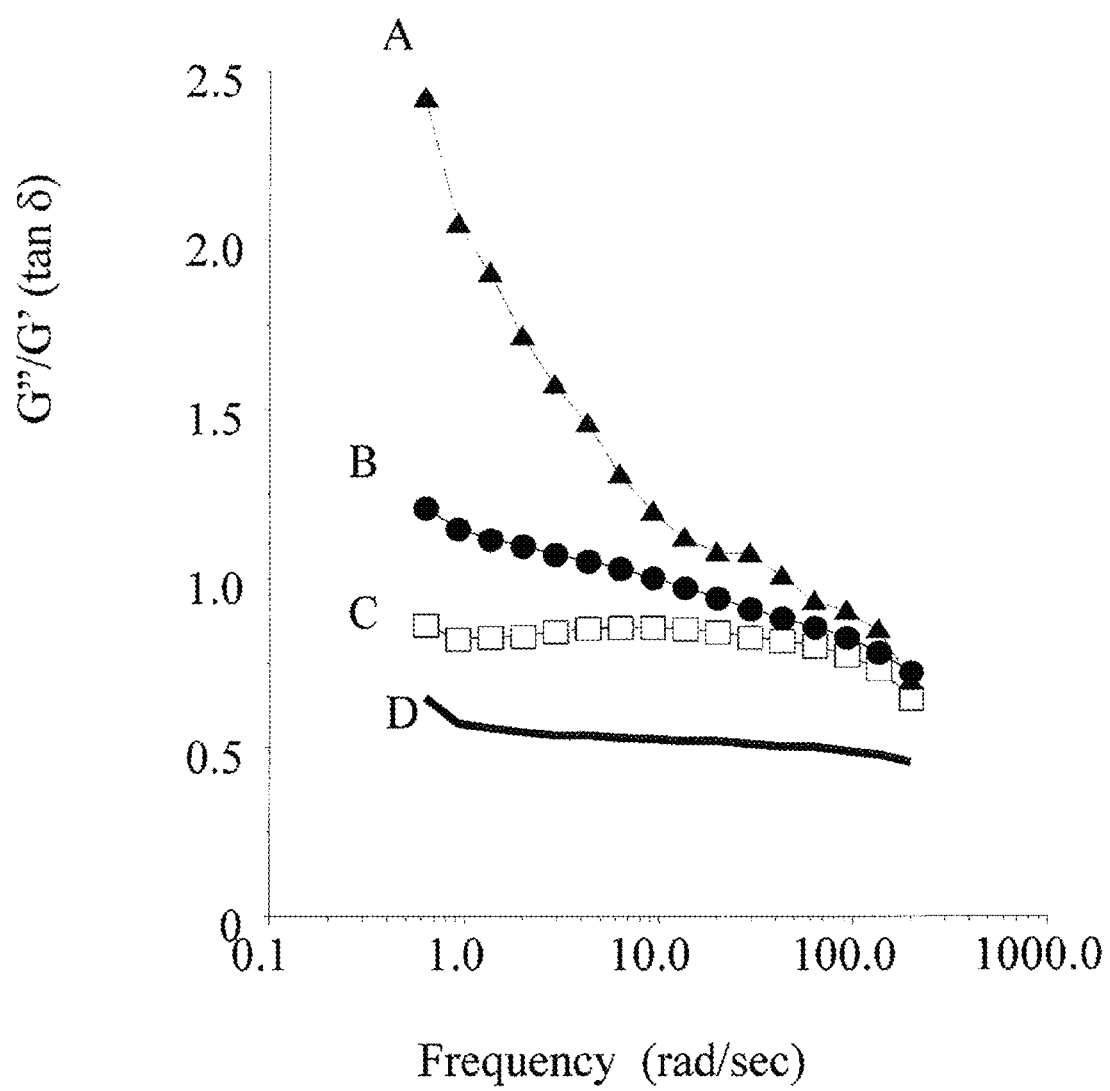
FIG. 3 is a graph depicting the ratio G"/G' (tan δ) vs. frequency for CMC/PEGDGE complexes cross-linked in the presence of NaOH catalysis of this invention.

Rheological properties of a 30 mg/ml solution in PBS were determined according to methods known in the art. Elasticities of these PEG/CMC compositions were increased dramatically as shown in FIG. 3 curve A and as described below.

Example 2

Crosslinking of CMC a with PEGDGE at a CMAG/Epoxide Ratio of 35.5/1 in Dilute NaOH To a 400 ml polypentene beaker, we added DIW (250 mL) and NaOH (10 g; 250 mM) with mechanical stifling. After 5 minutes of stifling at 400 rpm, we then added CMC A (7.5 g; 67.3 mM OH) and stirring continued for 35 minutes at 25° C. Subsequently, we added PEGDGE (0.23 g; neat; 0.2 mL; 0.87 mM) and stifling continued at ambient temperature for 90 minutes then heated to a temperature of about 70° C. for 3 hours then cooled to ambient temperature overnight.

The solution was then diluted to a volume of about 250 mL with DIW and neutralized with glacial acetic acid to a pH of 6. The resulting polymer was precipitated with IPA, collected and then ground in a blender with MEOH 250 ml. The granular solid was collected and washed three times with about 50 mL of MeOH, then dried in a hood for 20 minutes, and the dried in vacuo at a temperature of about 60° C.

Rheological properties of a 30 mg/ml solution of this material is shown as curve C in FIG. 3. FIG. 3 depicts a graph of G"/G' ratio (tan δ) vs. frequency for the reaction products of CMC A with PEGDGE in 1% NaOH solution at CMAG/EP ratios of 0.8, 2.4, 25.6, and CMC with no EP. The line with filled triangles (▲), A, is the tan δ vs. frequency for the reaction product with the CMAG/EP ratio of 0.8, the line with the filled circles (●), B, is the tan δ vs. frequency for the reaction product with the CMAG/EP ratio of 2.4, the line with the un-filled squares ( ) C, is the tan δ vs. frequency for the reaction product with the CMAG/EP ratio of 35.6, and the solid line with no symbol (–), D, is the tan δ for un-reacted CMC with no EP. The data clearly indicates that the un-reacted CMC has the lowest tan δ or is the most elastic material. In this case, all of the derivatized gels have higher tan δ than un-reacted CMC and as the CMAG/EP ratio is decreased from 25.6 to 2.4 to 0.8 the tan δ is increasing and the material is becoming less elastic. Since the elasticity of the gels decreases upon reaction with PEGDGE, this indicates that the CMC is decorated and not crosslinked with PEGDGE in the NaOH catalyzed reaction. By reacting CMC with PEGDGE in base, the tan δ of the CMC/PEG gels can be controlled by adjusting the CMAG/EP ratio.

Figure 4:
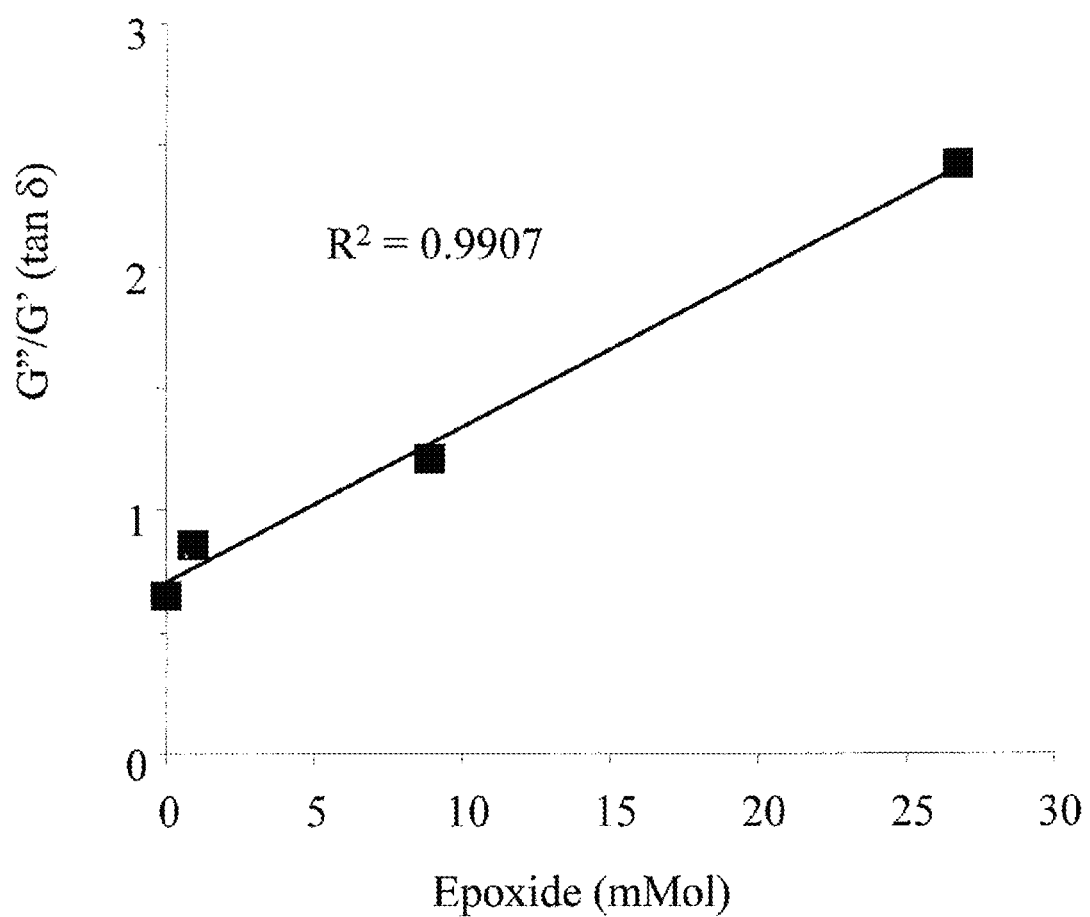
FIG. 4 is a graph depicting the effect of epoxide equivalents on tan δ for CMC/PEGDGE complexes of this invention having different ratios of CMAG/EP.

FIG. 4 depicts a graph of G"/G' (tan δ) at 0.628 rad/sec versus the amount of Epoxide (in mM) of CMC/PEG compositions shown in FIG. 3. As the epoxide equivalents increased, and the CMAG/EP ratio decreased, the tan δ increased and the CMC/PEO gel became less elastic. There was an excellent correlation between the tan δ of the gel and the epoxide equivalents contained in the gel ($R^2$=0.9907).

Figure 5:
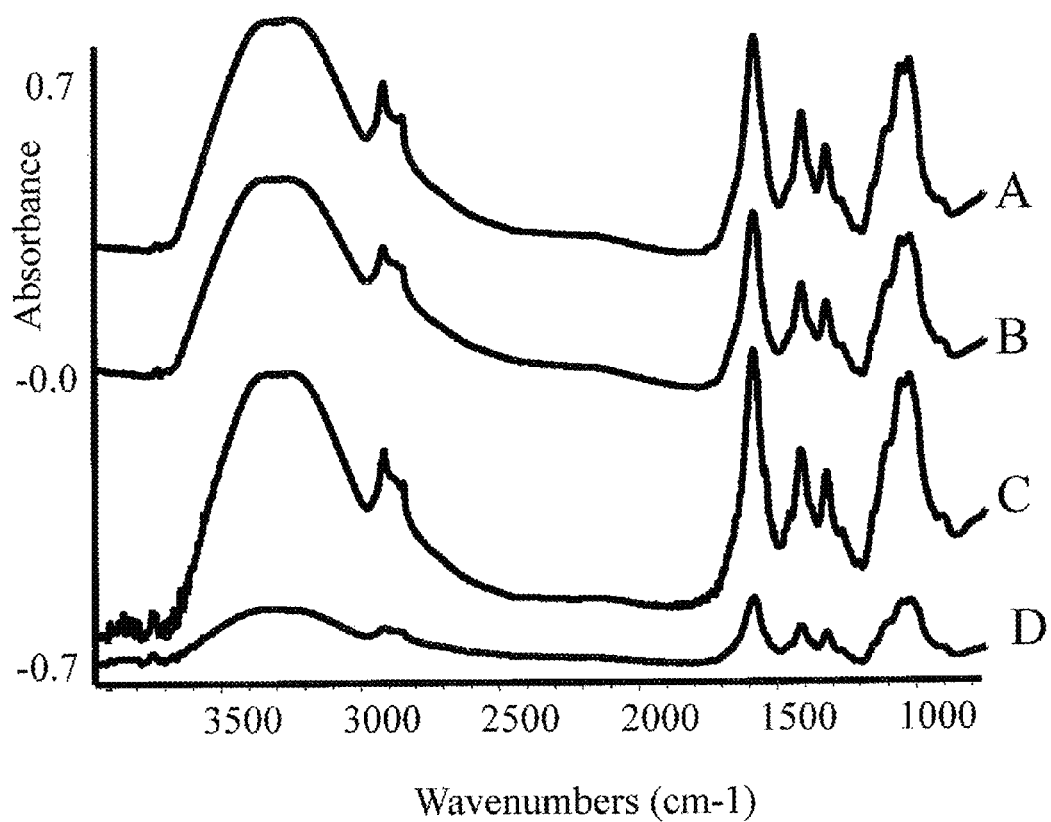
FIG. 5 depicts Fourier Transform Infra Red (FTIR) spectrograms of CMC/PEGDGE complexes of this invention formed under basic conditions in the presence of NaOH. Curves A, B, C and D represent spectra of complexes having different ratios of CMAG/EP.

FIG. 5 depicts FTIR spectra of the PEG/CMC gels from reaction of CMC A with PEGDGE at different CMAG/EP ratios. Graph A is of a PEG/CMC composition where the CMAG/EP ratio was 2.4. Graph B depicts the FTIR spectrum of material having a CMAG/EP ratio of 0.8. Graph C is the FTIR spectrum of material having a CMAG/EP ratio 35.6. Graph D is the FTIR spectrum of un-reacted CMC. For all of the compositions shown, very little ester was formed. We conclude from this series of studies that under NaOH catalyzed conditions, CMC and PEG form cross-linked polymers dominantly via ether linkages.

Example 3

Crosslinking of CMC a with PEGDGE at a CMAG/Epoxide Ratio of 1.78/1 in Dilute $NH_4OH$ In this example, to a 400 ml polypentene beaker we added DIW (250 mL) and 20% $NH_4OH$ (5 ml) under constant stifling for 5 minutes at 400 rpm. The resulting solution had a pH of 11. To this solution, we added CMC A (7.5 g; 67.3 mM OH) with constant stirring at 700 rpm for 35 minutes at a temperature of 25° C. At this time, PEGDGE (2.3 g; neat 2 mL; 8.7 mM) was added and stirring continued at ambient temperature for 2 hours and then another 2 ml (8.7 mM) of PEGDGE was added and stifling continued for a further 2 hours. The solution was then neutralized with dilute HCl to pH 6.8 and the polymer was precipitated with IPA and collected. The solid was ground in a blender with MeOH and the granular solid was collected and wash three times with about 50 mL of MeOH then dried in a hood for 20 minutes and the dried in vacuo at a temperature of about 60° C.

Figure 6:
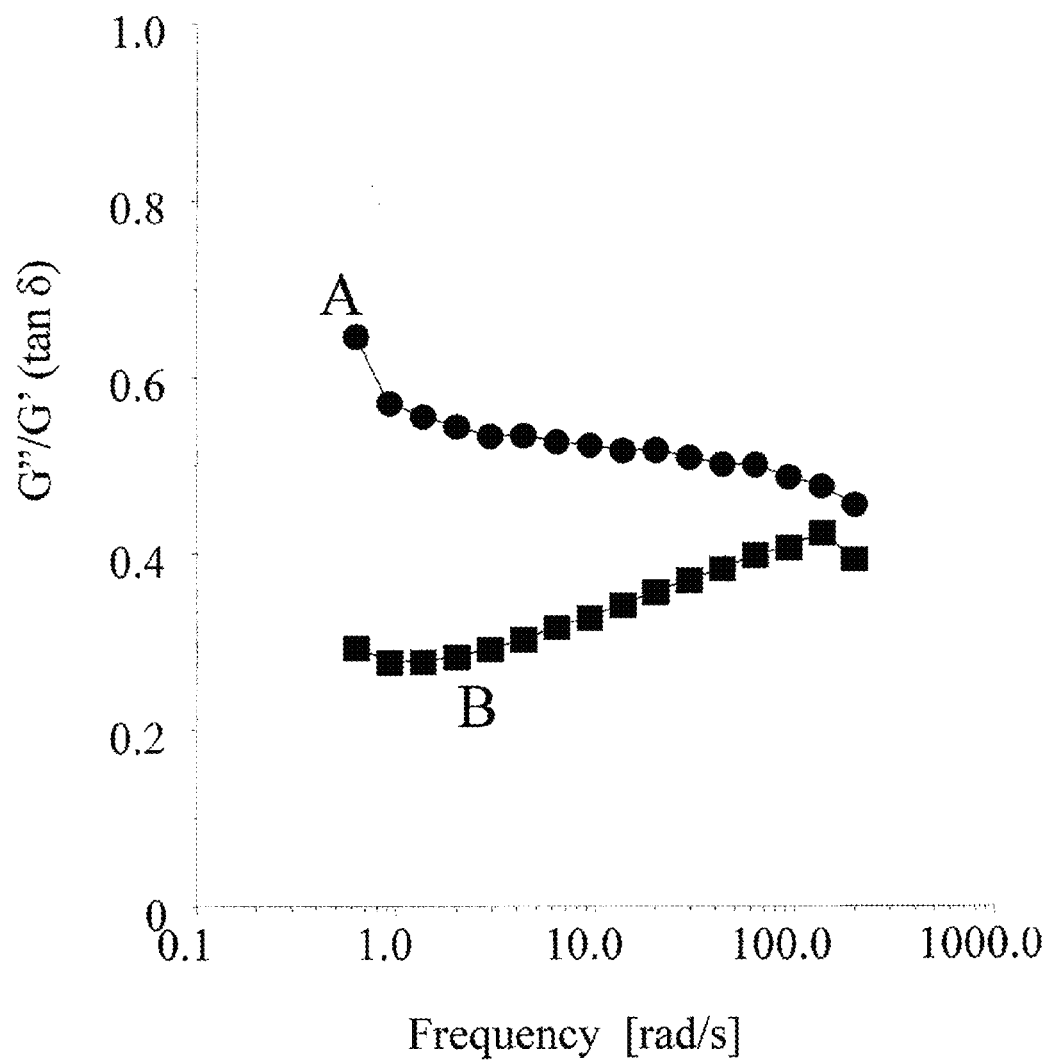
FIG. 6 depicts a graph of tan δ vs. frequency of CMC/PEGDGE complexes of this invention cross-linked under basic catalysis in the presence of NH$_4$OH.

FIG. 6 depicts graphs of tan δ vs. frequency for un-reacted CMC A (filled circles; ●; graph A) and a gel made with PEG/CMC produced by reacting CMC A and PEGDGE with a CMAG/EP ratio of 3.57 with base catalysis in the presence of dilute $NH_4OH$, filled squares (■; B). The $NH_4OH$ catalyzed reaction produced a highly elastic gel that has a much lower low frequency tan δ than un-reacted CMC A.

Figure 7:
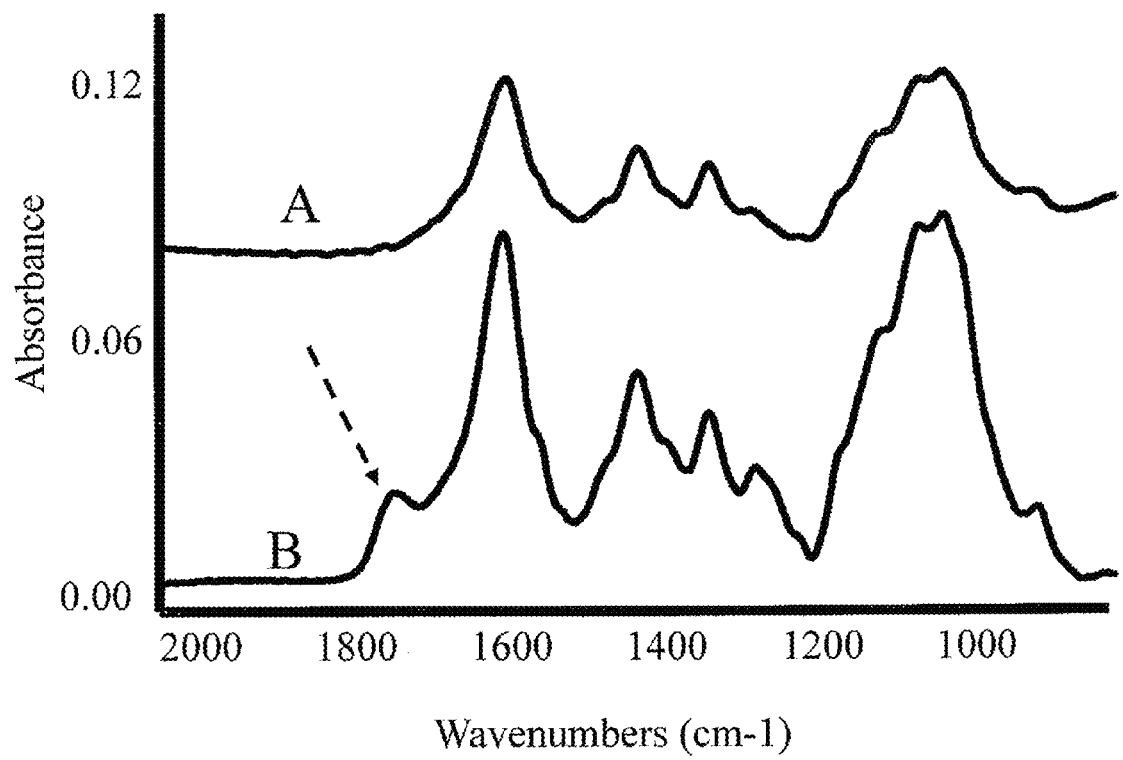
FIG. 7 depicts a graph of FTIR spectrograms for CMC alone (graph A), or CMC/PEGDGE (graph B). The complexes were cross-linked under basic catalysis in the presence of NH$_4$OH, showing the characteristic shoulder of ester linkages in graph B (arrow).

FIG. 7 depicts FTIR spectra of a 30 mL solution of this composition in PBS. un-reacted CMC A (graph A), and a PEG/CMC gel formed under base catalysis using dilute $NH_4OH$ of CMC and PEGDGE (graph B). Graph B clearly shows the presence of ester formation with a peak at about 1730 $cm^{-1}$ (dashed arrow).

Example 4

Crosslinking of CMC a with PEGDGE at a CMAG/Epoxide Ratio of 3.6/1 in Dilute Acetic Acid To a 400 ml polypentene beaker we added DIW (250 mL) and glacial acetic acid (HOAc) (2.5 ml; 49 mM). After 5 minutes of stifling at 400 rpm, CMC A (7.5 g; 67.3 mM OH) was added, and stirring continued for 55 minutes at ambient temperature. At this time PEGDGE (2.85 g; 2.5 mL; neat; 5.4 mM) was added and stifling continued at ambient temperature (about 40° C.) for 5 hours and the stirring stopped and the solution set in at room temperature for 70 hours.

The concentrated mass was diluted with 200 mL of DIW and precipitated with IPA (300 ml). The entire mass was ground in a blender with 250 mL of MeOH, and the solid was then suction filtered, washed with acetone, dried in the hood, and further dried at a temperature of 60° C. in a vacuum oven.

Figure 8:
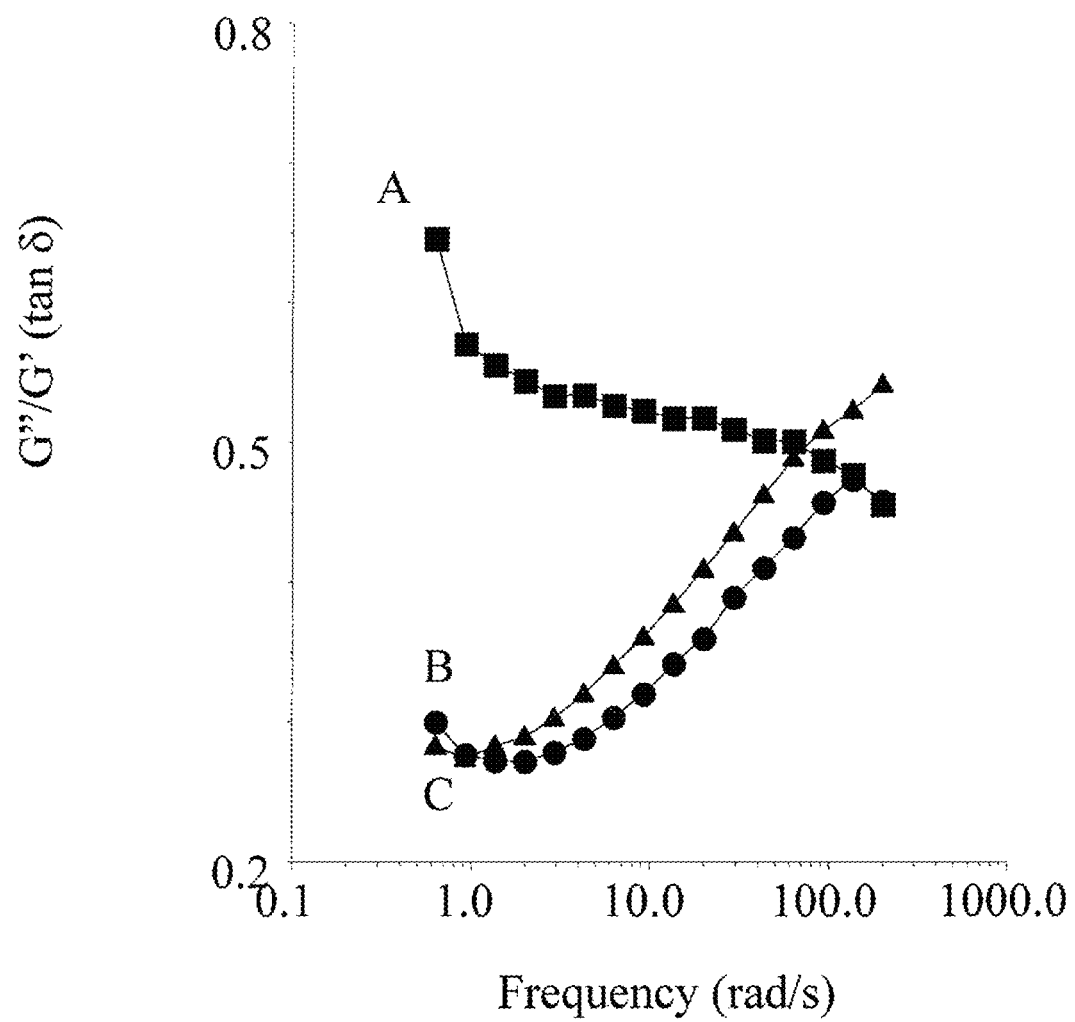
FIG. 8 depicts graphs of tan δ vs. frequency of CMC A and CMC/PEGDGE complexes of this invention, cross-linked under acidic catalysis and having different ratios of CMAG:EP.

Rheological properties of these materials are shown in FIG. 8 and described below.

Example 5

Crosslinking of CMC a with PEGDGE at a CMAG/Epoxide Ratio of 14.3/1 in Dilute Citric Acid In this series of studies, to a 600 ml polypentene beaker, we added DIW (250 mL) and citric acid (2.5 g) with constant stirring. After 5 minutes of stirring at 400 rpm, CMC A (7.5 g; 31 mM) was added, and stifling continued for 55 minutes at ambient temperature. At this time PEGDGE (2.85 g; neat; 0.5 mL; 1.1 mM) was added and stirring was continued at a temperature of 60° C. for 5 hours. After this time, the stifling was stopped and the solution set at room temperature for 70 hours. The concentrated mass was diluted with 200 mL of DIW, neutralized to pH 6.8 with dilute NaOH, and polymer was precipitated with IPA (300 ml). The entire mass was ground in a blender with 250 mL of MeOH, and the solid was then suction filtered, washed with acetone, dried in the hood, and further dried at a temperature of 60° C. in a vacuum oven.

The rheology data of a 30 mg/ml solution in PBS indicates that the elasticity of the cross-linked material has increased, curve C FIG. 8.

FIG. 8 depicts graphs of G"/G' ratio (tan δ) vs. frequency for reaction products of un-reacted CMC A, solid squares (■; graph A) CMC/PEGDGE reacted in 1% acetic acid with a CMAG/EP ratio of 3.6, solid circles (●; graph B), and CMC/PEGDGE reacted in 0.01% citric acid with a CMAG/EP ratio of 14.3, solid triangles (▲; graph C). The acid catalyzed reactions produced gels that were more elastic than the un-reacted CMC at low frequency. In this case, adjusting the CMAG/EP ratio to between 3.6 and 14.3 produced gels that had the same low frequency tan δ of about 0.3. The acid catalyzed reaction between CMC and PEGDGE appeared to be crosslinking and not decorating the CMAG units. We found that the elasticity of the cross-linked material was increased compared to un-derivatized CMC.

Figure 9:
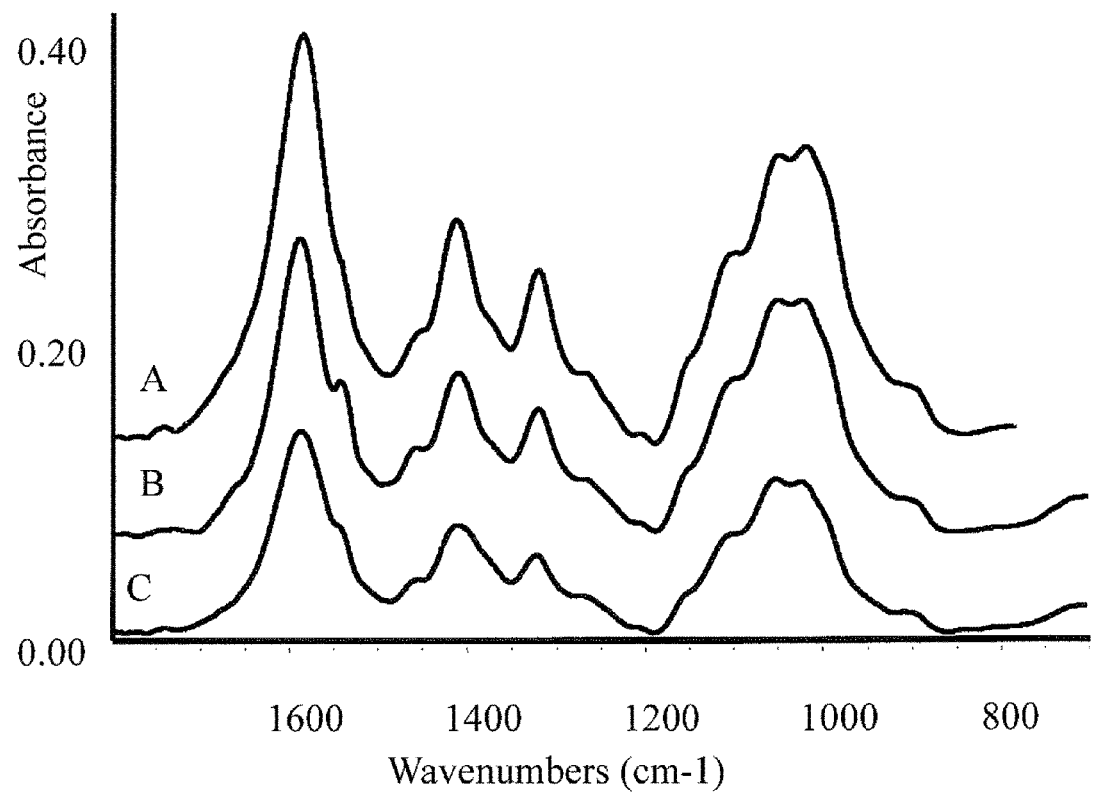
FIG. 9 depicts FTIR spectra of acid catalyzed reaction products of CMC A with PEGDGE. Graph A is of un-reacted CMC A and graph B is of CMC A/PEGDGE reacted in 1% acetic acid with a CMAG/EP ratio of 3.6. Graph C is of CMC A/PEGDGE reacted in 0.01% citric acid with a CMAG/EP ratio of 14.3.

FIG. 9 depicts FTIR spectra of the acid catalyzed reactions of CMC A with PEGDGE. Graph A depicts the FTIR spectrum of un-reacted CMC A, graph B depicts the FTIR spectrum of CMC A/PEGDGE reacted in 1% acetic acid with a CMAG/EP ratio of 3.6, and graph C depicts the FTIR spectrum of CMC A/PEGDGE reacted in 0.01% citric acid with a CMAG/EP ratio of 14.3. These spectra are all very similar and show very little ester peak. We conclude that the cross-linking under acidic catalysis with acetic acid produces products linked dominantly via ether linkages.

Example 6

Crosslinking of CMC B with PEGDGE at a CMAG/Epoxide Ratio of 4.7/1 in Dilute Acetic Acid In this series of studies, to a 600 ml polypentene beaker, we added DIW (250 mL) and stirred in glacial acetic acetic acid (2.5 ml). After 5 minutes of stirring at 400 rpm, the pH was 4. Subsequently, CMC B (12.5 g; 51.7 mM) was added and stirring continued at 700 rpm for 35 minutes at a temperature of 25° C. At this time, PEGDGE (2.93 g; neat; 2.5 mL; 5.56 mM) was added and stifling continued at ambient temperature for 2 hours and then the temperature was increased to about 60° C. for 3 hours. The solution was then cooled to room temperature and set overnight. The concentrated mass was diluted with 200 mL of DIW, neutralized to pH 6.8 with dilute NaOH, and precipitated with IPA (300 ml). The entire mass was ground in a blender with 250 mL of MeOH, and the solid suction filtered, washed with acetone, dried in the hood, and further dried at a temperature of 60° C. in a vacuum oven.

Figure 10:
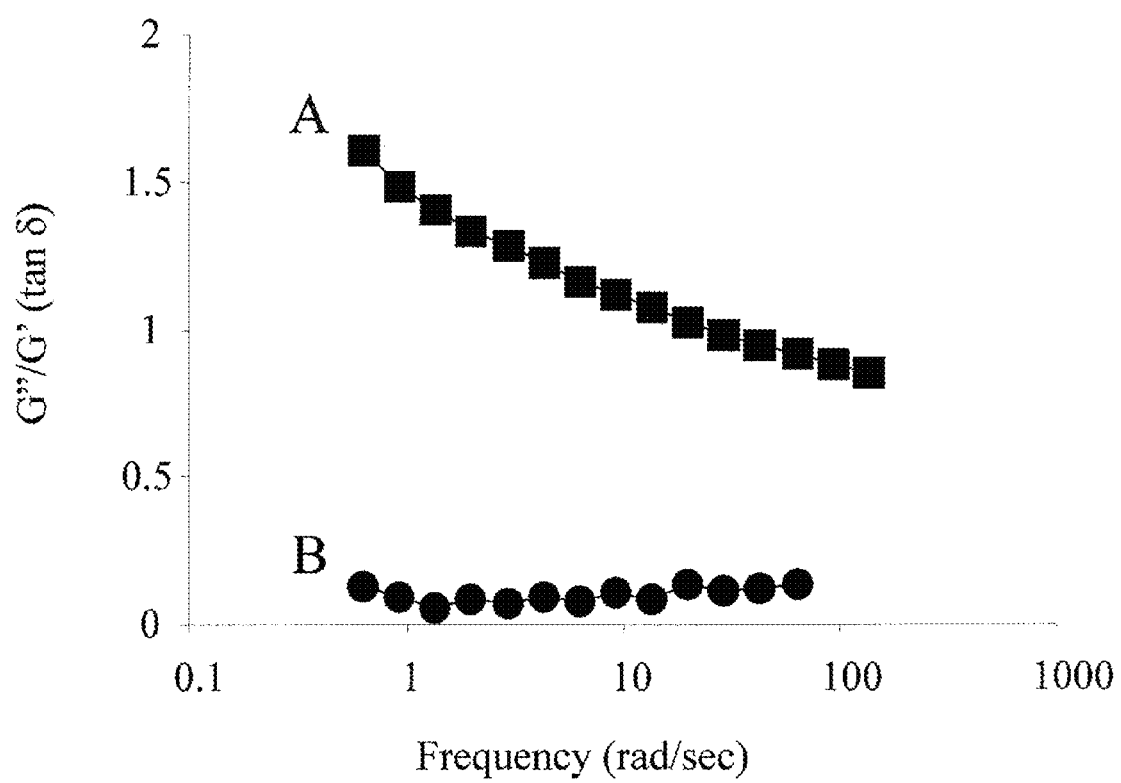
FIG. 10 depicts tan δ vs. frequency of un-reacted CMC B (graph A) and CMC B/PEGDGE complexes of this invention, cross-linked under acidic catalysis and having a ratio of CMAG/EP of 5.1:1 (graph B).

The elasticity of a 3% solution of this material in PBS is shown in FIG. 10. FIG. 10 depicts graphs of tan δ vs. frequency for un-reacted CMC B (solid squares ■; graph A) and for CMC B reacted with PEGDGE in 1% acetic acid at a CMAG/EP ratio of 5.1/1 (solid circles ●; graph B). The CMC/PEGDGE gel (graph B) is highly elastic (i.e., has a lower tan δ, indicating that CMC has been cross-linked with PEGDGE.

Figure 11:
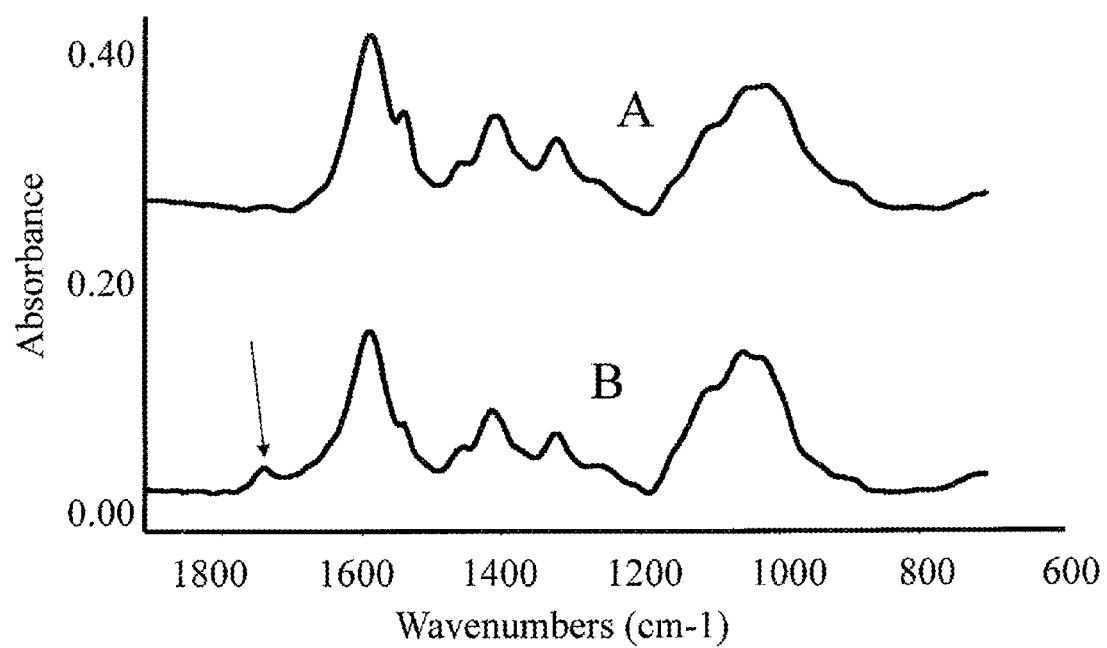
FIG. 11 depicts FTIR spectra of CMC and CMC/PEGDGE complexes of this invention, cross-linked under acidic catalysis and having ratio of CMAG/EP of 5.1:1.

FIG. 11 depicts FTIR spectra of un-reacted CMC B (graph A) and CMC B reacted with PEGDGE in 1% acetic acid at a CMAG/EP ratio of 5.1 to 1 (graph B). The cross-linked CMC/PEGDGE material has some ester formation indicated by the arrow at about 1730 cm$^{-1}$ We conclude from these studies that under these conditions, CMC and PEGDGE react with each other to produced a cross-linked polymer having at least some ester linkages.

Example 7

CMC/Multi-Branch PEG Compositions

Figure 12:
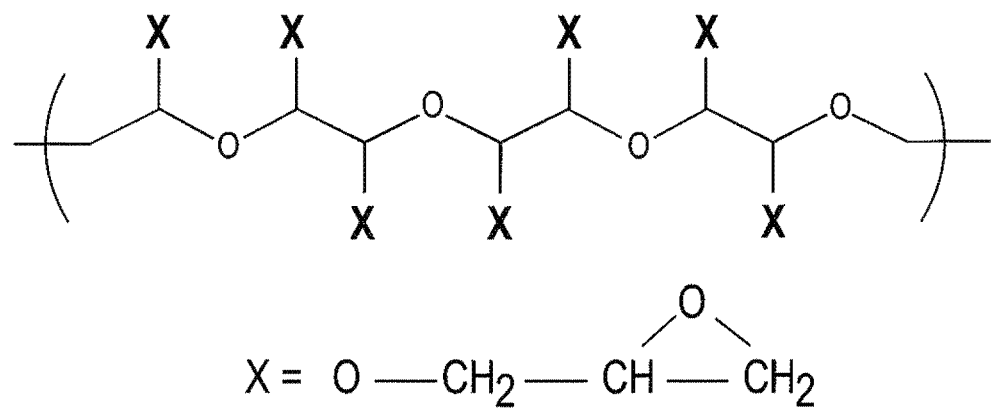
FIG. 12 depicts a multi-branched PEG-epoxide useful for manufacturing compositions of this invention.

Compositions of CMC with greater cross-linking can be created using PEGs that are multi-branched. Such PEGs are available from SunBio (Orinda, Calif.), and are depicted in FIG. 12. FIG. 12 depicts a chemical structure of a PEG, in which each of the in-chain carbon atoms has an epoxide residue attached thereto. Such a PEG has an epoxide:ethylene oxide ratio of 2:1. However, one can use PEGS that are not fully substituted with epoxide moieties. Rather, one can use PEGs with different ratios of epoxide:ethylene oxide. Thus, altering the number of epoxide moieties on multi-branch PEGs can be be used to provide increased choices, along with the use of CMC or other CPSs having different degrees of substitution.

To make a cross-linked CMC/multi-branch PEG composition according to this example, methods as disclosed in Example 1 can be used. A CMC is selected, a multi-branch PEG is selected, a solution of the CMC is made in aqueous solution and the multi-branch PEG is introduced and the reaction is permitted to proceed.

We find that increasing the number of epoxide residues on a multi-branch PEG increases the amount of cross-linking, increases the residence time and increases the elasticity of the composition.

Example 8

CMC Compositions Containing Multi-Arm PEGs

Figure 13:
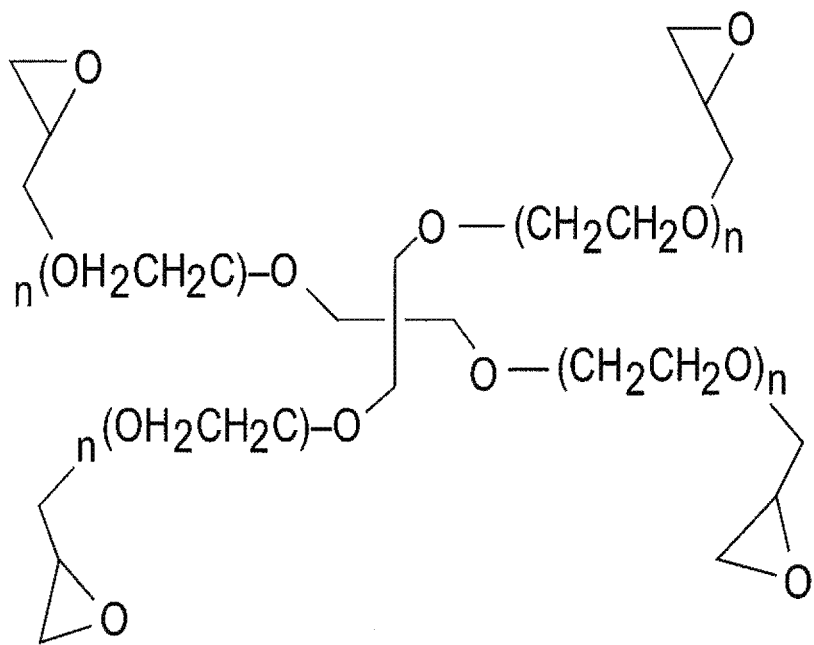
FIG. 13 depicts a multi-arm PEG-epoxide useful for manufacturing compositions of this invention.

To provide additional compositions, CMC and multi-arm PEGs can be used to create cross-linked compositions. A multi-arm PEG is a molecule containing more than one PEG molecule, each of which contains at least one epoxide moiety. Generally, multi-arm PEGS have a core molecule. In the case of a 4-arm PEG, the core can be penta-erythritol. For 6-arm PEGs, hexose backbones can be used. In both cases, the core molecule provides reactive groups that can be covalently bonded to PEG molecules. In the case of a penta-erythritol core, the resulting 4-arm PEG has a structure shown FIG. 13.

To make a CMC/PEG cross-linked composition using a multi-arm PEG, one uses methods described in Examples 1 or 7. A CMC is selected and prepared in aqueous solution. Then a multi-arm PEG is selected and introduced into the CMC solution. The reaction is permitted to proceed, and the cross-linked CMC/PEG composition is then isolated.

Example 9

Uses of Multi-Arm PEG and Multi-Branch PEG/CMC Compositions

CMC/PEG compositions described in Examples 7 and/or 8 can be used in situations in which a stronger cross-linking is desired. CMC/multi-arm PEG or CMC/multi-branch PEG compositions are used to increase permanence of the composition for filling excavating voids in internal tissues and the skin. Such compositions can polymerize at higher rates than PEGDGE because of the increased number of reactive epoxide moieties present.

By selecting PEGs having increased number of epoxide moieties and/or lower molecular weights (e.g., lower numbers of ethylene oxide moieties), the polymerization rates, tissue residence times and elasticities of CMC/PEG compositions can be increased. Similarly, selecting a CMC having a higher degree of substitution can produce CMC/PEG compositions having higher polymerization rates, tissue residence times and elasticities.

Example 10

Uses as Replacements for Intervertebral Disk Nucleus I

In situations in which it is desirable to provide a vertebral disk nucleus replacement, a CMC/multi-branch PEG or CMC/multi-arm PEG composition can undergo an in situ polymerization reaction. Thus, a composition having a relatively low viscosity can be implanted into a vertebral space. Subsequently, a polymerization reaction can occur, thereby providing a cross-linked, highly elastic composition that can be weight bearing and therefore can reduce symptoms usually associated with extrusion or degeneration of a disk nucleus.

Example 11

Cross-Linking of CMC C with PEGDGE at a CMAG/Epoxide Ratio of 2.3:1 in Dilute Citric Acid with Steam Sterilization In this example, we wished to determine if a PEG/CMC composition could be made without precipitation and reconstitution before use. We therefore carried out a series of studies using CMC/PEGDGE mixtures loaded into syringes without carrying out these steps. We compared the elasticity of such a material with a CMC/PEO composition containing calcium ions. Such calcium/CMC/PEO compositions are described in U.S. Pat. No. 6,869,938, incorporated herein fully by reference.

We dissolved calcium chloride (0.04 g) and sodium chloride (0.313 g) in 50 mL of a solution containing 0.01% citric acid in a 100 mL beaker with mechanical stirring. We then slowly added solid CMC C (1.804 g; 7.45 mM) over about 2 minutes. After 5 minutes of stirring, we then added PEGDGE (0.75 mL; 0.855 g neat; 3.25 mM) and the mixture was stirred for 2 hours at room temperature. The homogeneous mixture was then loaded into 3 mL polypropylene syringes and placed into sterilization pouches and steam sterilized in an autoclave for 32 minutes at 122° C. and cooled overnight to room temperature.

Figure 14:
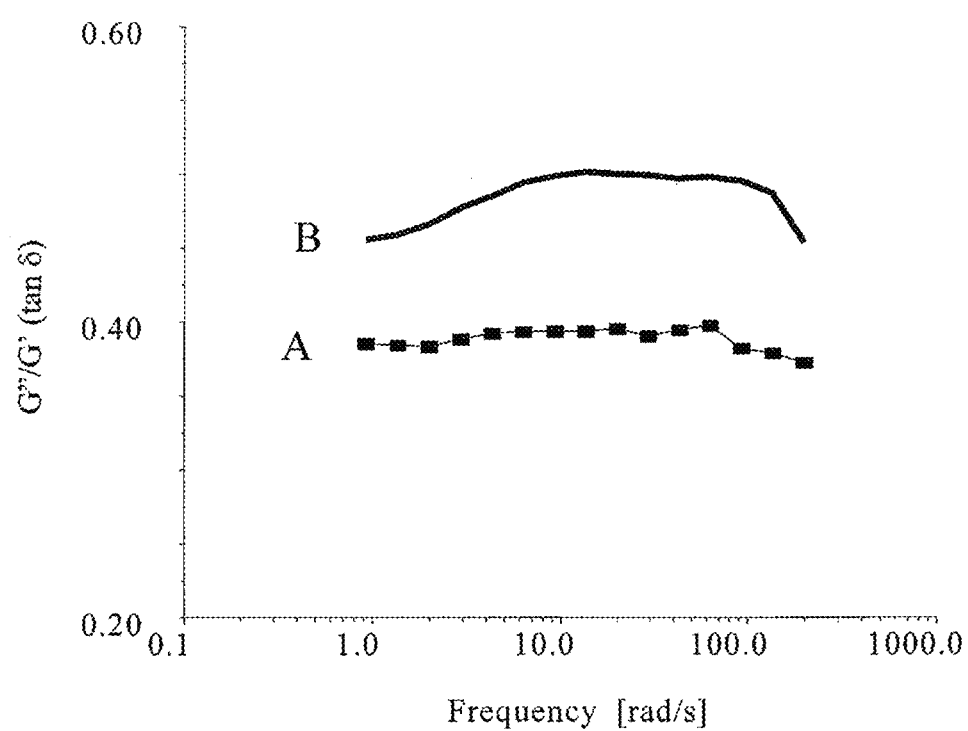
FIG. 14 depicts a graph of tan δ vs. frequency for two gels, one (graph A) made with CMC C and polyethylene oxide (PEO) and heat-sterilized, and another (graph B) made with CMC C and PEGDGE and subsequently heat sterilized.

The rheology of this CMC/PEGDGE gel was compared to the rheology of a CMC gel without PEGDGE prepared as above is shown in FIG. 14. FIG. 14 depicts graphs of G"/G' (tan δ), vs. frequency for two different gels. Graph A (solid squares) depicts results for a gel produced from CMC C reacted with PEGDGE in 0.01% citric acid with $CaCl_2$ and NaCl and steam sterilization with a CMAG/EP ratio of 2.3. Graph B (solid line) depicts results for a gel produced from CMC C and non-functional PEO dissolved in DIW with $CaCl_2$ and NaCl that was steam sterilized. We conclude that the covalently cross-linked CMC/PEGDGE gel has greater elasticity than the CMC/PEO ionically cross-linked material, especially at low frequencies.

Example 12

Uses as Replacements for Intervertebral Disk Nucleus II

A patient presents with damage or degeneration of a nucleus of an intervertebral disk. The patient is anesthetized and a portion of the spinal column is revealed. To produce a load-bearing structure in the intervertebral space, a biologically compatible spherical or cylindrical sac is inserted in a deflated condition through a small hole in the annulus and into the intervertebral space of a patient in need thereof. Once in place, a PEG/CMC composition of this invention of this invention is introduced into the sac. Then, the PEG/CMC composition is permitted to polymerize into an elastic, load-bearing structure.

Figure 16A:
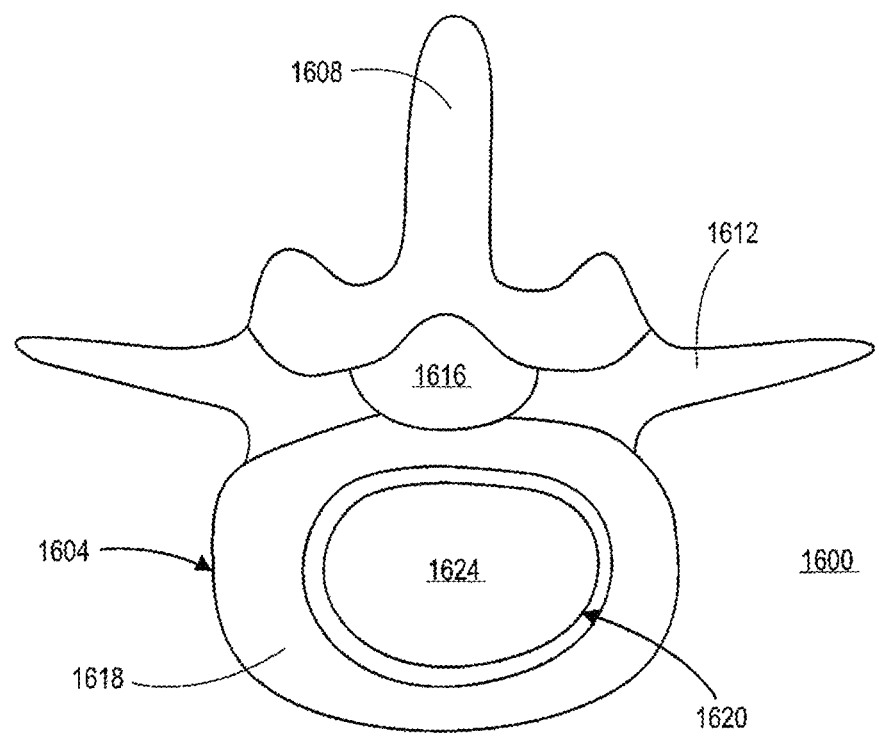
FIGS. 16a and 16b depict views of vertebrae with a PEG/CPS composition in a bag as a replacement for the nucleus pulposus surrounded by an annulus.
Figure 16B:
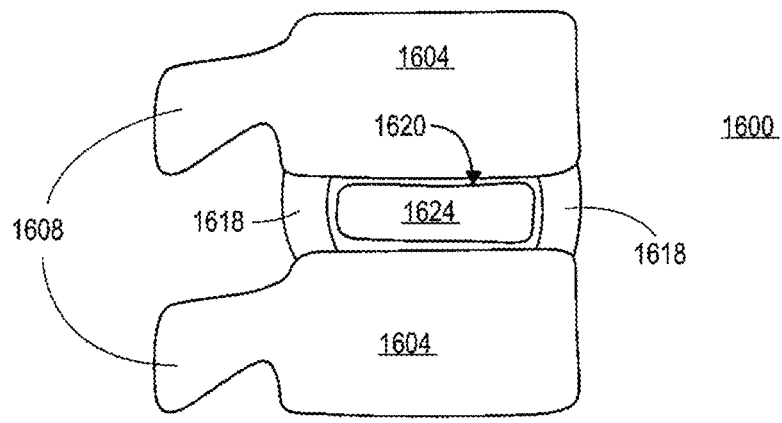

FIGS. 16a and 16b depict use of compositions of this invention as a partial or complete replacement for a nucleus pulposus. FIG. 16a depicts a top view of embodiment 1600 of this invention. A vertebra has a vertebral body 1604, a dorsal spinous process 1608, lateral spinous processes 1612, and a spinal canal 1616 (where the spinal cord is located). As shown, annulus 1618 surrounds the space where the nucleus has been lost. However, within annulus 1618, a bag 1620 containing a PEG/CPS composition 1624 of this invention has been placed.

FIG. 16b depicts a lateral cross-sectional view of the embodiment 1600 of this invention as shown in FIG. 16a. Two adjacent vertebrae are shown. Vertebral bodies 1604 are show connected together by annulus 1618. Dorsal spinal processes 1608 are depicted for orientation. The nucleus has been lost, and in its place, bag 1620 is shown filled with a PEG/CPS composition 1624 of this invention.

Example 13

Uses as Replacements for Intervertebral Disk Nucleus III

A patient presents with damage or degeneration of a nucleus of an intervertebral disk. The patient is anesthetized with local or general anesthetics and a portion of the spinal column is revealed. The location of the damage is located, and the annulus is evaluated for integrity. If there is no satisfactory hole in the annulus, a small incision in the annulus is made. Multiple PEG/CPS-filled sacs are introduced in either inflated or deflated conditions, depending on the size of a hole in an annulus of a patient in need thereof. Where the annulus is intact, a small hole is made in the annulus and a plurality of cylindrical or spherical sacs is introduced into the intervertebral space. The longitudinal axis(es) of a cylindrical sac is aligned parallel to the direction of the load, and the sacs are then filled with a PEG/CPS composition of this invention, and the compositions permitted to polymerize.

Figure 17A:
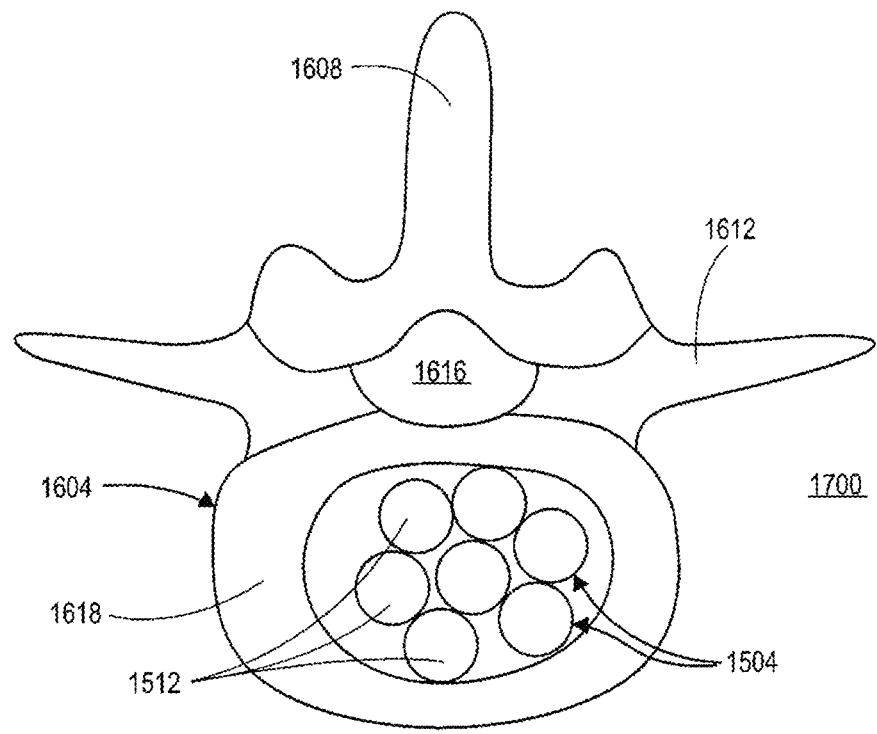
FIGS. 17a and 17b depict views of vertebrae with a plurality of PEG/CPS-filled bags within an annulus, wherein the plurality of bags is a replacement for the nucleus pulposus.
Figure 17B:
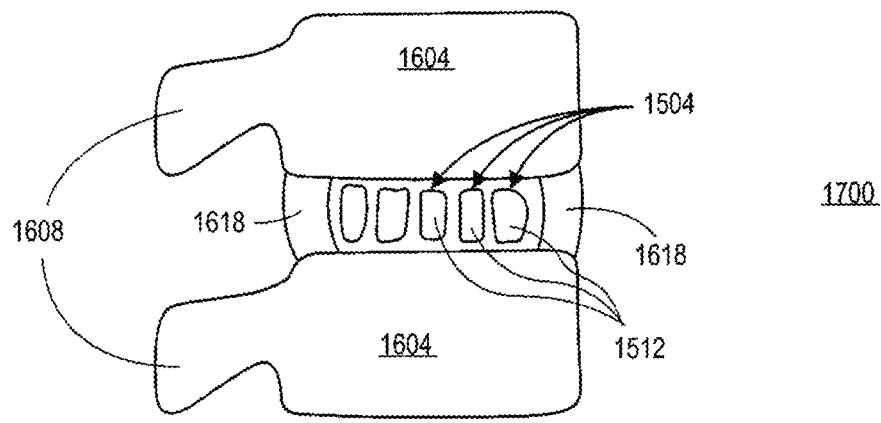

FIGS. 17a and 17b depict an alternative embodiment 1700 of this invention. FIG. 17a depicts a top view of a vertebra having vertebral body 1604, dorsal spinal process 1608 and lateral spinous processes 1612. Spinal canal 1616 is depicted. Annulus 1618 is shown and in the location from where the nucleus had been lost has a plurality of small bags having exteriors 1504 and filled with PEG/CPS compositions 1512 of this invention.

FIG. 17b depicts a lateral cross-sectional view of the embodiment 1700 as shown in FIG. 17a. Two adjacent vertebrae are shown. Vertebral bodies 1604 of each vertebra are shown connected to each other via annulus 1618, defining a space there in where the nucleus pulposus has been lost. A plurality of bags with exteriors 1504 are shown filled with PEG/CPS composition 1512 of this invention.

Example 14

Uses as Replacements for Intervertebral Disk Nucleus IV

A patient presents with damage or degeneration of a nucleus of an intervertebral disk. The patient is anesthetized with local or general anesthetics and a portion of the spinal column is revealed. The location of the damage is located, and the annulus is evaluated for integrity. If there is no satisfactory hole in the annulus, a small incision is made and one or more cylindrical sacs are introduced into the intervertebral space, within the annulus. Once so introduced, each sac is then filled with a PEG/CPS composition of this invention. Then, a larger deflated sac is introduced into the intervertebral space and is situated near the hole in the annulus. Once positioned, a PEG/CPS composition of this invention is introduced into the sac and is permitted to polymerize. This "plug" sac then remains within the annulus and plugs the hole in the annulus to minimize the extrusion of the smaller sacs through the hole.

Figure 18:
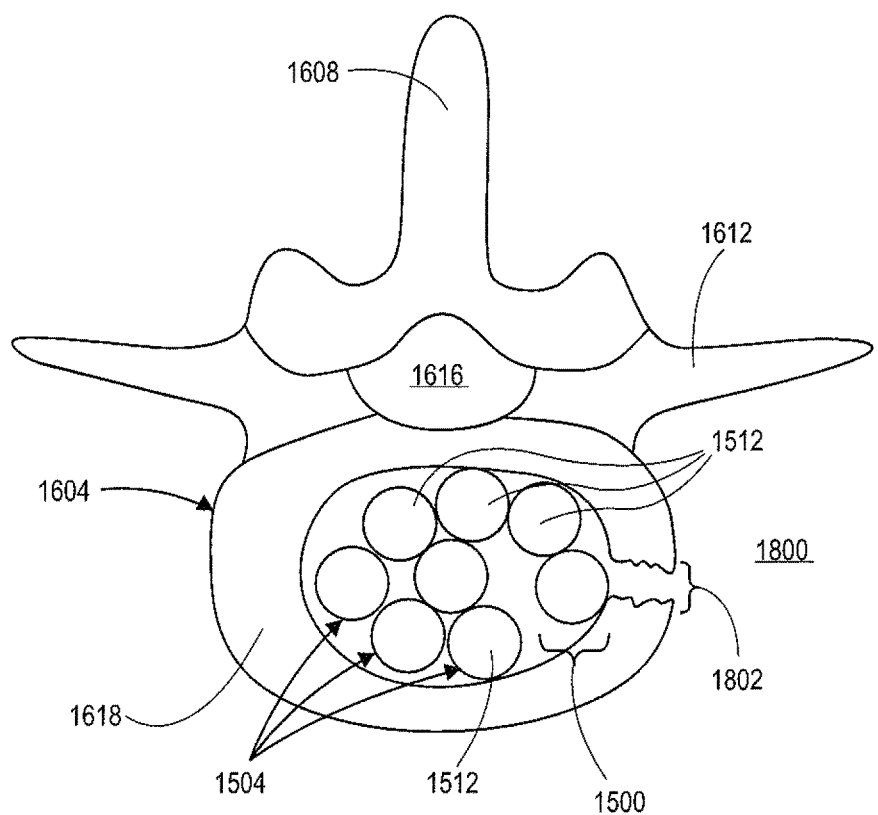
FIG. 18 depicts a top view of an embodiment of this invention in which an intervertebral space has an annulus having a defect and showing a plurality of PEG/CPS-filled bags therein, with one bag occluding the defect.

FIG. 18 depicts a top view of an alternative embodiment 1800 of this invention. A vertebra is shown having vertebral body 1604, dorsal spinal process 1608 and lateral spinous processes 1612. Spinal canal 1616 is also shown. Annulus 1618 is depicted having a defect or hole 1802. Also shown is a plurality of bags having exteriors 1504 filled with PEG/CPS composition 1512 of this invention. Also depicted is PEG/CPS-filled bag 1500 shown occluding defect 1802, thereby decreasing the likelihood that the bags will be extruded.

It can be appreciated that in the above examples, either a spherical, cylindrical, or other closed shape can be used.

The examples above are provided for purposes of illustrating specific embodiments of this invention. Persons of ordinary skill can readily produce other embodiments based on the teachings of this application without undue experimentation. All such embodiments are included within the scope of this invention. All references cited herein are incorporated fully by reference, as is separately so incorporated.

We claim:

1. A method of using a PEG/CMC composition, comprising the steps:
   providing a PEG/CMC composition comprising:
      a carboxymethyl cellulose-A (CMC-A) having a molecular weight of about 700,000 Daltons and a degree of substitution of about 0.65 to 0.85; and
      a polyethylene glycol diglycidyl ether (PEGDGE) having a molecular weight of about 500 Daltons, said PEG linked to said CMC via a base catalyzed addition reaction in the presence of $NH_4OH$, where the ratio of CMC repeat units (CMAG) to epoxide units is in the range of 0.5 to 30, the composition having significant ester bonding structure, and where the elasticity of said composition is greater than the elasticity of CMC-A alone; and
   introducing said composition into a portion of a subject's body in need thereof.

2. The method of claim 1, wherein said need is for space filling.

3. The method of claim 1, wherein said need is to inhibit formation of tissue-tissue adhesions.

4. The method of claim 1, wherein said need is for drug delivery.

5. The method of claim 2, wherein said composition is introduced into the skin via a needle.

6. The method of claim 1, wherein said need is for filling a bone void.

7. The method of claim 6, wherein said bone void is in the intervertebral space and said composition is introduced into the intervertebral space.

8. The method of claim 1, wherein said PEG/CMC composition is applied to a tissue at risk for developing an inflammatory reaction.

9. The method of claim 1, wherein said PEG/CMC composition is introduced into the intervertebral space.

10. A method of using a PEG/CMC composition, comprising the steps:
   providing a PEG/CMC composition comprising:
      a carboxymethyl cellulose-A (CMC-A) having a molecular weight of about 700,000 Daltons and a degree of substitution of about 0.65 to 0.85; and
      a polyethylene glycol diglycidyl ether (PEGDGE) having a molecular weight of about 500 Daltons, said PEG linked to said CMC via a base catalyzed addition reaction in the presence of $NH_4OH$, where the ratio of CMC repeat units (CMAG) to epoxide units is in the range of 0.5 to 30, the composition having significant ester bonding structure, and where the elasticity of said composition is greater than the elasticity of CMC-A alone; and
   lubricating a medical instrument with said composition.

\* \* \* \* \*